United States Patent
Gellman et al.

[11] Patent Number: 6,099,547
[45] Date of Patent: Aug. 8, 2000

[54] METHOD AND APPARATUS FOR MINIMALLY INVASIVE PELVIC SURGERY

[75] Inventors: Barry N. Gellman, Easton; David Sauvageau, Methuen, both of Mass.; Rodney Brenneman, San Juan Capistrano, Calif.; Armand A. Morin, Berkeley, Mass.; William Pintauro, Ft. Lauderdale, Fla.; Rodney Appell, Shaker Heights, Ohio

[73] Assignee: SCIMED Life Systems, Inc., Maple Grove, Minn.

[21] Appl. No.: 09/023,533

[22] Filed: Feb. 13, 1998

Related U.S. Application Data

[60] Provisional application No. 60/038,380, Feb. 13, 1997.

[51] Int. Cl.$^7$ .................................................. A61M 29/00
[52] U.S. Cl. ............................................ 606/198; 606/167
[58] Field of Search .................................. 606/167, 196, 606/198, 205, 206, 207, 208, 209

[56] References Cited

U.S. PATENT DOCUMENTS

| | | | |
|---|---|---|---|
| D. 275,790 | 10/1984 | Marlowe | D24/27 |
| D. 319,877 | 9/1991 | O'Neal-Cox | D24/143 |
| 2,253,132 | 8/1941 | Malson | 32/63 |
| 2,400,251 | 5/1946 | Nagel | 128/361 |
| 2,631,585 | 3/1953 | Siebrandt | 606/205 |
| 3,580,313 | 5/1971 | McKnight | 145/46 |
| 3,657,744 | 4/1972 | Ersek | 3/1 |
| 4,156,424 | 5/1979 | Burgin | 128/18 |
| 4,254,763 | 3/1981 | McCready et al. | 128/20 |
| 4,617,916 | 10/1986 | LeVahn et al. | 128/20 |
| 4,945,897 | 8/1990 | Greenstein et al. | 128/20 |
| 5,026,376 | 6/1991 | Greenberg | 606/96 |
| 5,027,793 | 7/1991 | Engelhardt et al. | 128/20 |
| 5,122,130 | 6/1992 | Keller | 606/205 |
| 5,174,278 | 12/1992 | Babkow | 128/17 |
| 5,308,349 | 5/1994 | Mikhail | 606/88 |
| 5,397,330 | 3/1995 | Mikhail | 606/88 |
| 5,536,251 | 7/1996 | Evard et al. | 606/205 |
| 5,562,679 | 10/1996 | Valtchev | 606/119 |
| 5,569,300 | 10/1996 | Redmon | 606/207 |
| 5,618,260 | 4/1997 | Caspar et al. | 600/210 |
| 5,681,265 | 10/1997 | Maeda et al. | 606/197 |
| 5,735,849 | 4/1998 | Baden et al. | 606/205 |
| 5,755,726 | 5/1998 | Pratt et al. | 606/205 |

FOREIGN PATENT DOCUMENTS

| | | |
|---|---|---|
| 610512 | 6/1978 | U.S.S.R. |
| WO 96/28083 | 9/1996 | WIPO |

OTHER PUBLICATIONS

International Serch Report for PCT/US98/03069.

*Primary Examiner*—Michael Buiz
*Assistant Examiner*—Daphna Shai
*Attorney, Agent, or Firm*—Testa, Hurwitz & Thibeault, LLP

[57] ABSTRACT

The invention provides a driver and methods for advancing needles, cannulas, and other medical devices through the pubic bone. The driver may be used in connection with a driver frame assembly for proper positioning and stabilization of the driver, and with other devices for creating a cavity in the urethral floor and for positioning medical devices therein. The invention also provides simple connections for attaching a suture to a device within the cavity in the urethral floor or in the vagina, and also for attaching sutures to the pubic bone.

5 Claims, 33 Drawing Sheets

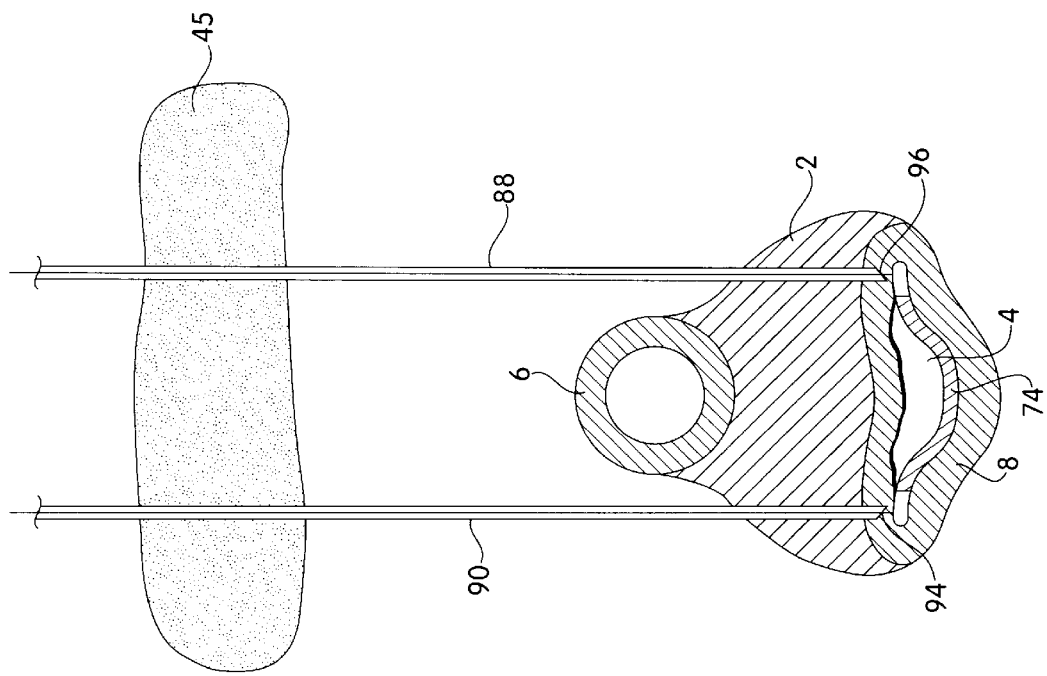
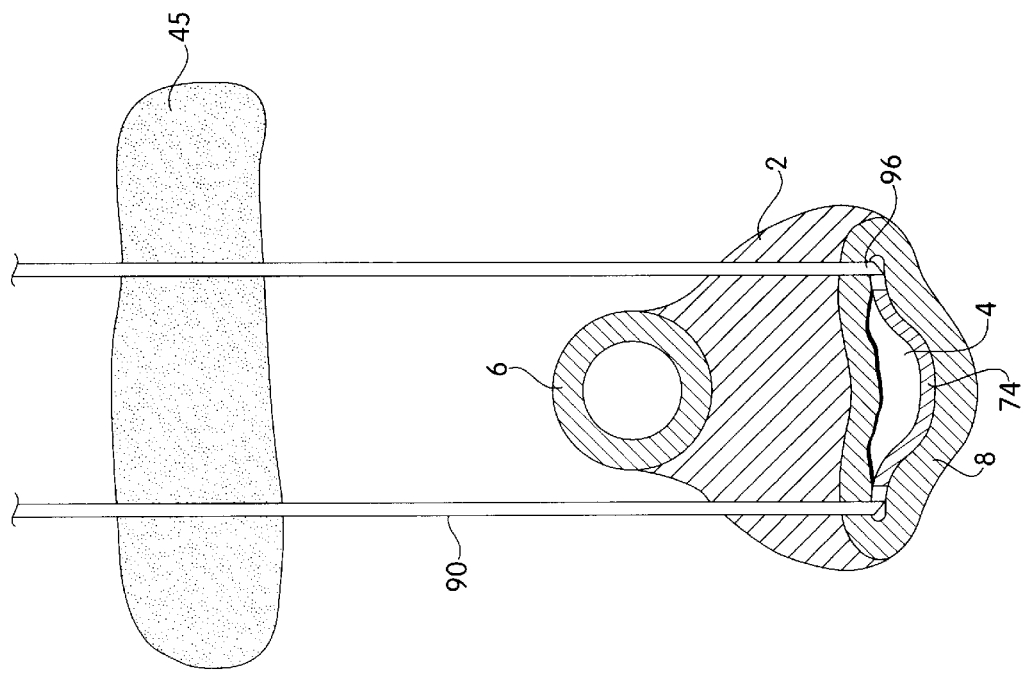

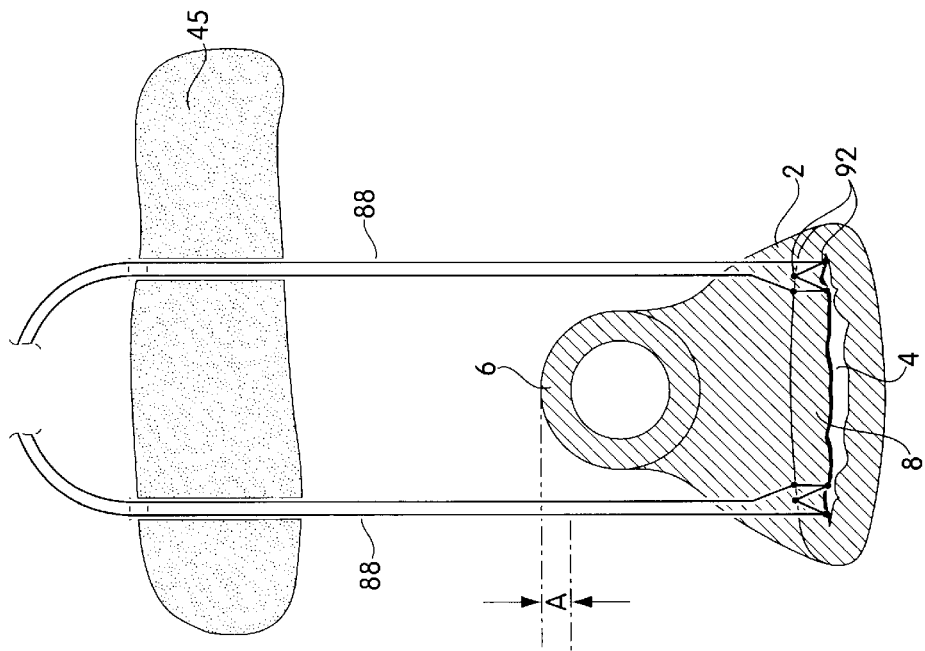
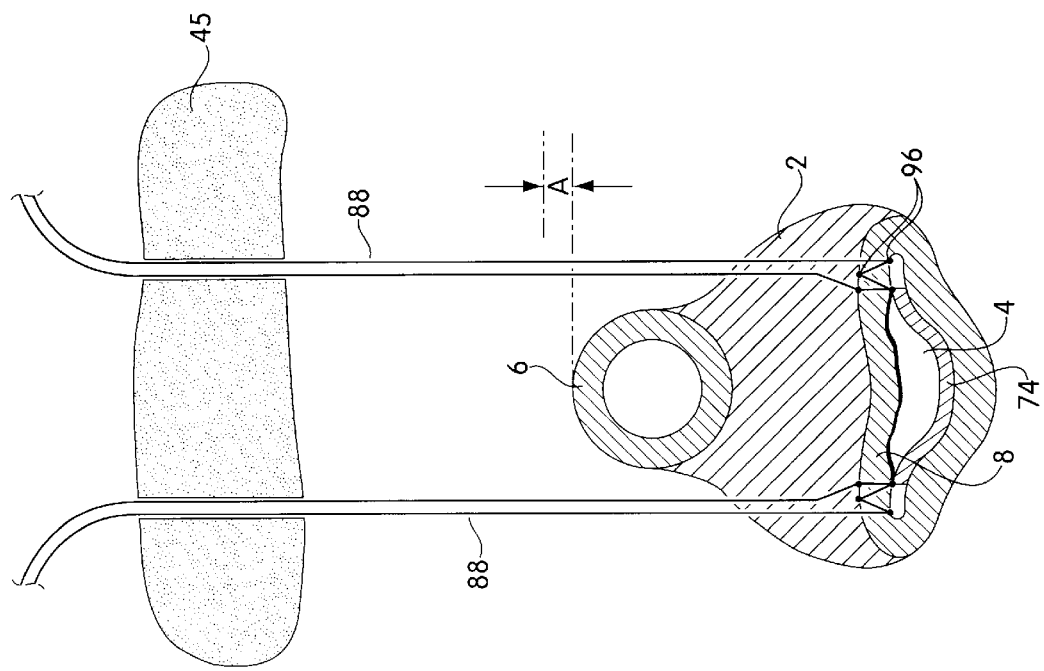

METHOD AND APPARATUS FOR MINIMALLY INVASIVE PELVIC SURGERY

RELATED APPLICATIONS

This application claims priority from U.S. Provisional Patent Application Ser. No. 60/038,380, filed Feb. 13, 1997.

FIELD OF THE INVENTION

The present invention relates to methods and devices for treating urinary incontinence. More particularly, the present invention relates to methods and devices for creating a cavity near the urethral floor, methods and devices for placement of a urethral sling or other device in such a cavity, and methods and devices for driving bone-piercing guides into and through the pubic bone for use in stabilizing the urethra or pelvic floor.

BACKGROUND OF THE INVENTION

The present invention relates to the treatment of stress urinary incontinence "SUI," and to improved methods and surgical devices for the surgical treatment of SUI. The devices disclosed herein are additionally useful in a wide variety of other surgical procedures.

Genuine stress incontinence is the involuntary loss of urine due to a sudden rise in intra-abdominal pressure. It has been estimated that between 40% and 50% of young, healthy nulliparous women admit to occasional mild stress incontinence; however, at least 80% of stress incontinence patients are in the perimenopausal age group and are multiparous. Raz has suggested that the female urethral continence mechanism is dependent on the interaction of four urethral factors: urethral closing pressure, urethral length, urethrotrigonal anatomy, and urethral reception of intra-abdominal pressure. Raz, S., Modified bladder neck suspension for female stress incontinence, *Urology*, 17:82, 1981.

The urethral closing pressure is predominantly a result of the interaction of smooth and striated muscle sphincter activity, but there is also some contribution by nonmuscular urethral factors such as the submucosal vascular plexus, the elastin and collagen content of the urethral tissues, and a sphincter like effect of the mucosa. There has been considerable diversity of opinion regarding the anatomic structure and the innervation of the urethral sphincters, and a variety of views have been expressed in the literature.

Urethral length is important in the maintenance of continence. However, although it certainly interacts with other factors to contribute to continence, a short urethra alone will not produce incontinence. Urethral length varies considerably in normal women, and women with proven genuine stress urinary incontinence do not invariably have urethral shortening.

Urethrotrigonal anatomy, which can be demonstrated by lateral cystourethrography, should fulfill certain criteria. The bladder base should lie above the level of the inferior ramus of the symphysis, and with straining should not descend more than 1.5 cm. There should be a normal urethrotrigonal alignment with an angle normally less than 100 degrees, and the urethral axis should be approximately 35 degrees from the vertical. In the hypermobile situation loss of all of the normal anatomic features may occur, a radiologic finding that correlates with the clinical finding of cystourethrocele. However, clinical experience has shown that the coexistence of cystourethrocele and incontinence does not predict that the incontinence is of a genuine stress variety.

The transmission of intra-abdominal pressure to the intra-abdominal portion of the proximal urethra is also reported to be important in the maintenance of continence. This is a passive phenomenon, and is the result of the normal anatomic configuration just described. Whenever there is a rise in intra-abdominal pressure during such stresses as coughing or straining, the pressure is transmitted not only to the bladder but also to the proximal urethra, with resultant increase in the closing pressure, and prevention of leakage. If the urethral axis is altered, rotational descent will drop the proximal urethra and bladder base from its intra-abdominal location, and will obviously impair such pressure transmission.

A wide variety of operations have been used to correct this condition, generally involving the principles of elevating the bladder neck anteriorly and/or elongating and narrowing the proximal urethra. Two of the most popular operations today for stress incontinence are the Marshall-Marchetti-Krantz and Birch vesicourethropexies. The Marshall-Marchetti-Krantz technique has at least an eighty-five percent success rate, against which other operative success rates must be measured. Recently, the Pereyra operation and its modifications have enjoyed some popularity, but less than basic techniques.

Notwithstanding the foregoing, however, there remains a need for an improved treatment for SUI. Preferably, the treatment is as noninvasive as possible under the circumstances, and will eliminate or minimize hospitalization and the use of general anesthetics. In addition, there remains a need for improved medical instrumentation such as tissue cavity dilators, incision guides, bone-piercing guide drivers, and quick-connect slings and suture-securing devices for use in connection with SUI treatment and other medical procedures. U.S. Pat. No. 5,611,515, issued Mar. 18, 1997 to Benderev et al., introduces pioneering minimally invasive percutaneous and transvaginal bladder neck stabilization approaches. The percutaneous approach of Benderev et al. involves stabilizing the bladder neck using a bone anchor which is percutaneously introduced from the abdominal side of the patient. The transvaginal approach of Benderev et al. involves stabilizing the bladder neck using a staple or bone anchor which is transvaginally placed into the pubic bone. The methods and devices of the present invention may be used in several urethral or bladder neck stabilization procedures that are less invasive than many of those currently available.

SUMMARY OF THE INVENTION

It is an objective of this invention to provide a means and method for relatively sterile placement of urethral slings. It is a further objective of this invention to provide an apparatus for straight line positioning for bone piercing, so as to achieve proper placement of urethral slings and to minimize difficulty in aligning a bone-piercing apparatus with the ultimate target in a tissue cavity. Another objective is to provide apparatus and a method for reconstructing and stabilizing the urethral or pelvic floor by affixing devices placed to support the urethral or pelvic floor to a fixed reference tissue such as a bone. A further objective is to provide improvements over current techniques that require drilling holes in a bone, and the placement of bone anchors therein.

This invention has the additional objective of providing rapid and simple surgical connections for connecting a suture to a medical device inside a tissue cavity or other structure in the body that may be in need of stabilization. This invention also seeks to provide alternatives to transvaginal methods of urethral and pelvic floor reconstruction and stabilization, to minimize the risk of infection, and to enable surgeons to approach the urethral or pelvic floor from different locations. Finally, it is a further objective to provide minimally invasive means and methods of securing a target tissue to an immoveable reference tissue, such as the pubic bone. One of more of these objectives is satisfied by various embodiments of the invention.

The invention provides a dilator for creating a cavity in tissue. The dilator has two functional portions: an insertion spreader and handles. The insertion spreader includes of two facing guides that may be semi-cylindrical. The spreader has open and closed positions. In the closed position the guides are close together and the dilator may have the appearance of a split tube or cylinder, while in the open position the guides are separated. In both positions the guides remain essentially parallel to each other.

The insertion spreader may be attached to the handles for manipulation of the guides. The handles can be joined together with a pivot, so that pivoting the handles translates to a movement of the guides either toward or away from one another. The dilator may also have a ratcheting lock for maintaining the insertion spreader in a fixed position. The penetrating ends of the guides also may be sharpened to facilitate penetrating the target tissue.

The dilator aspect of the invention also provides a method of creating a tissue cavity by using the dilator. With the insertion spreader in the closed position the spreader is advanced into the target tissue. When the spreader reaches the desired depth the handles are moved to separate the guides. The separation of the guides causes a tearing of the tissue, creating a cavity therein. This method also may be employed by first advancing a needle partially into the tissue to create an insertion path. The guides of the spreader are positioned about the protruding part of the needle and inserted into the tissue along the same path created by the needle.

This method for spreading tissue with the dilator of the invention may be used to create a cavity in the vaginal hiatus. The term "vaginal hiatus" refers to the tissue between the urethra and the vagina. This term may apply to the exterior surface between the distal urethra and the vaginal orifice as well as to the deeper tissue between the urethra and the upper vaginal wall. In some cases spreading may be facilitated by performing an episiotomy of the skin of the vaginal hiatus. The method of this aspect of the invention also may be performed transvaginally to create a cavity, for example in the vaginal wall. Whatever the tissue, the method may be preceded with a fluid-dissection of the target tissue, wherein a solution is injected into the tissue to create a fluid bolus. The fluid bolus forms a pocket in the tissue, and the dilator is used to create an opening connecting the outer surface to the pocket.

The invention also provides an insert card for advancing a medical device, for example a urethral sling, into a tissue cavity. One end of the card holds the sling to be used for stabilizing tissue or internal structures of the urethral or pelvic floor. The other end of the card is fashioned to permit a physician to grasp and manipulate the card, or to align or connect the card with other external devices, such as those disclosed herein. The sides of the card may be adapted for use with the dilator mentioned above. Thus the card can be used to enhance both the sterility and the positional precision in a sling-placement procedure.

The card and the dilator may thus be used in a method of advancing a sling into a tissue cavity. The tissue cavity is created by the dilator as described above, and the spreader is locked in the open position. A sling is placed in the proper position on the card, and the card is positioned so that its lateral edges align with and slide into the spreader guides. The spreader guides provide a track for the insertion of the card to the desired depth within the cavity. This method of sling placement may be used in procedures employing a variety of techniques for securing the sling, including techniques adapted for slings that are to be secured with sutures, quick connect devices, bone anchors, staples, and the like.

Also provided in this invention is an incision guide for creating a cavity between the urethra and the vagina. The incision guide has a catheter that is inserted into the urethra. This catheter expands and straightens the urethra, essentially immobilizing the urethra in an easily identified position. Also part of the incision guide is a cutter that slides along the catheter and makes an incision into the vaginal hiatus that is a fixed distance from, and therefore parallel to, the urethra. The catheter may display graduation marks or other indicia to enable a surgeon to determine the position of the catheter or the cutter relative to the bladder neck.

The incision guide of the invention may also have a stop, such as a block or a ring, that locks in place on the catheter. The stop abuts the cutter and prevents insertion of the cutter beyond the desired depth of incision.

The cutter portion of the incision guide may be a needle, a blade, a bipolar knife, or other incision device adapted for slidably mounting to the rigid catheter. One example of such an adapted incision device is the dilator of the invention as described above.

The incision guide aspect of the present invention provides a method of creating a cavity in the vaginal hiatus. The method includes the steps of inserting the catheter into the urethra, determining the position of the bladder neck by using the catheter, and inserting the attached cutter into the vaginal hiatus. The catheter allows straight-line tracking for the cutter and indicates the depth of incision, thus avoiding injury to the bladder.

This method of creating a cavity in the vaginal hiatus may be used in concert with the method of placing a sling in a cavity by use of the card, as discussed above. The card supporting the sling may advance into the cavity having its edges in contact with the hiatal tissue along the sides of the cavity. Alternatively the dilator of the invention also may be used to serve as a guide for the card, after the cavity is made using the incision guide of the invention. When the card reaches the intended depth in the cavity, the sling is in proper position for fastening in place.

An additional aspect of the present invention provides a driver for driving a guide into or through the pubic bone. The driver has two jaws and a slide bar. The first jaw has a distal end that inserts into a tissue cavity and a proximal end that attaches to the slide bar. The second jaw slides along the slide bar toward the first jaw. The second jaw has a bone-piercing guide attached to it such that the guide moves toward the first jaw when the second jaw is advanced along the slide bar. The guide connected to the driver may be a cannula, a needle, or a like device adapted for driving through bone.

The driver provides a method of driving a guide through the pubic bone. The steps include: inserting the first jaw of the driver into a tissue cavity, locating the pubic bone, positioning the driver to align the pubic bone between the first jaw and the second jaw, and advancing the second jaw toward the first jaw to drive the guide through the pubic bone.

The invention further provides a method for passing a device through the pubic bone. The guide is driven through the pubic bone as outlined above. The guide is next retracted, leaving a path through the bone, and the device is passed through the pubic bone along the path made by the guide. The device passed by this method may be a suture, a suture passer, a quick-connect fastening device, and the like.

In an additional method of this aspect of the invention, the driver of the invention is used to advance a cannula through the pubic bone. The lumen of the cannula constitutes a channel through the pubic bone. A device may then be passed through the bone within the lumen of the cannula. Devices that may be passed by this method include a suture, a suture passer, a quick-connect fastening device, and the like.

A further method of pelvic surgery provided by the invention includes the following steps. A cannula is driven through the pubic bone with the driver of the invention. The cannula is further driven into the tissue cavity in which the first jaw of the driver is positioned. The first end of a suture is passed through the cannula and secured to a structure within the cavity. The second end of the suture is secured to the pubic bone, thereby stabilizing tissue adjacent to the cavity. According to this method, the cannula may be removed from the bone before either end of the suture is secured, or the suture within the tissue cavity may be secured before withdrawal of the cannula. The suture within the tissue cavity may be secured by stitching the suture through a tissue mass of the cavity, or by attaching the suture to a structure introduced into the cavity for stabilizing the tissue of the cavity, such as a suture button.

The invention also provides a method of pelvic surgery wherein a cannula is driven through the pubic bone and into the tissue cavity as described above, and a suture is passed through the cannula and into the cavity. The suture is passed through a structure therein to stabilize the tissue adjacent to the cavity, then the suture is passed back out along the same path through the bone, and both ends of the suture are secured to the pubic bone.

Yet another method of the invention involves driving a cannula through the pubic bone and into a tissue cavity in a first location to make a first path. The suture is then advanced into the cavity along the first path. The suture is passed through a structure of the cavity to stabilize the tissue adjacent to the cavity. The cannula is then driven through the bone and into the cavity along a second path, and the suture is withdrawn from the cavity along the second path. Both ends of the suture are then secured to the pubic bone.

The foregoing methods focus on the path of the suture: the suture may be advanced one-way into the cavity and affixed there, or the suture may be advanced and withdrawn from the cavity along the same path through the bone, or the suture may be advanced and withdrawn along two separate paths through the bone. Regardless which method is used, the tissue cavity of the method may be the vagina. Alternatively, the cavity may be a hiatal cavity made according to a method of the dilator or incision guide aspects of the present invention. Further, the tissue cavity of the method may be a transvaginally created pocket into the plane of the vaginal hiatus. Also regardless which method is used, the method may advantageously be performed on the left side of the cavity and on the right side of the same cavity by piercing the pubic bone on both sides lateral to the pubic symphysis. The method may also include a step of tensioning the suture to elevate or otherwise stabilize the tissue mass.

Further provided is a method of stabilizing a urethral sling relative to the pubic bone. This is done by creating a tissue cavity and creating a path through the pubic bone by driving a guide through the bone. Then a urethral sling is placed into the cavity. A suture is passed through the pubic bone along the path, and is attached to the tissue mass. The suture is then secured to the pubic bone to stabilize the tissue.

Another aspect of the invention provides a driver frame assembly for positioning and stabilizing a bone-piercing guide driver relative to the patient. The driver frame assembly includes an upper clamp and a lower clamp, as well as a catheter, a cavity tongue, and the driver. The upper clamp has a head portion, a descending arm, and a base portion. The head portion has a compression foot for compressing the patient's abdominal surface against the pubic bone. Stabilizing pins extend downward from the compression foot and penetrate the abdominal surface adjacent to the superior surface of the pubic bone. The base portion of the upper frame attaches to the catheter and the tongue. The catheter is used to expand and straighten the urethra; the tongue inserts into the cavity, providing counterpressure to oppose the pressure of the compression foot. The lower clamp has a buttock plate for insertion beneath the patient, so that the patient's weight rests on the plate to secure the frame assembly relative to the patient. The lower clamp also has an ascending arm that connects with the base portion of the upper clamp. Finally, at least one driver is attached to the descending arm of the upper clamp. There may be more than one driver mounted to the frame assembly, or there may be one driver that drives two bone-piercing guides, which may be displaced to the left and right of center relative to the patient.

This aspect of the invention provides a method for stabilizing pelvic tissue by relatively non-invasive pelvic surgery. The foregoing frame assembly is installed on the patient. The bone-piercing guide is positioned and is driven through the bone and into the cavity. A stabilizing device is passed along the path through the bone created by the guide and secured in the cavity, thus stabilizing the targeted tissue of or adjacent to the cavity. This method may employ two or more guides, or one guide in various positions, to create more than one path through the pubic bone. The path created may be directly through the bone, after removal of the guide, or may be through the guide itself, if the guide is a cannula.

The stabilizing device thus passed through the bone may be a suture, a suture passer, a quick connect device, and the like. The cavity may be the vagina, a cavity of the vaginal hiatus, or a cavity made by entry through the vaginal wall. The method of stabilization may be a suture stitching of the cavity tissue or the placement of a quick connect device to a sling or suture button. The tissue stabilization is achieved by securing the suture to the bone with a quick-connect bone suture fastener. A sling, suture button, or like device that attaches to the suture or quick connect may be positioned in the tissue cavity by using the card discussed above in cooperation with the frame. The tongue of the frame may be adapted to cooperate with the card much like the dilator of the invention, such that the proper placement of the tongue as part of frame installation assures proper positioning of the device to be carried on the card for binding the device to a suture or a quick connect device. This card may be advanced into position in a cavity of the vaginal hiatus, the vagina, or a cavity made in the vaginal wall.

Another aspect of the invention provides a system for attaching a urethral sling to a suture. The system includes a urethral sling and a connector. Part of the sling is a ring member. The ring member has a central opening that cooperates with the sling to allow unidirectional passage of the connector through the opening, and to prevent retrograde passage of the connector through the opening. The connector and ring member may have a variety of configurations. One such configuration provides a ring member having several flanges and a substantially conical connector with a shoulder that contacts the flanges, preventing withdrawal of the connector from the ring member. Another configuration provides a connector having an elongate axial segment and a leading segment that is flexibly perpendicular to the axial segment. This "T" connector may cooperate with a ring member that is simply an opening in the urethral sling. The connectors of any configuration may be a attached to a suture.

This aspect of the invention provides a method for securing a sling for urethral and pelvic floor reconstruction. A sling having a suitable ring member is placed in position in a tissue cavity. A suture with a suitable connector is passed through the pubic bone, and the connector is advanced through the ring member of the sling. The suture is then fastened to the pubic bone, thus securing the sling in the cavity. The cavity may be the vagina, a cavity of the vaginal hiatus, or a cavity in the vaginal wall.

A closely related aspect of the invention provides a system for attaching a securing device to a suture. The system includes a securing device with a ring member, and a connector that attaches to a suture. The ring member and the connector cooperate as described above. The securing device may be a suture button, a staple, or a quick connect.

The method provided in this aspect of the invention is a method for securing a target tissue to the pubic bone. The securing device with a ring member is placed within or adjacent to the target tissue. A suture with a suitable connector is passed through the pubic bone, and the connector is advanced through the ring member of the securing device. The suture is fastened to the pubic bone, thus securing the target tissue to the bone.

Also part of the present invention is a bone eyelet having a sleeve and at least one crosspiece. The sleeve has an outer surface and an inner surface. The outer surface is adapted for inserting into a bone, and the crosspiece is attached to the inner surface to transect the sleeve, providing a plurality of channels in the sleeve. The crosspiece may be a plane or a rod. Alternatively, the crosspiece may be created by a piercing or crimping of the sleeve. The sleeve may have an external friction surface for contacting with the bone. It may have a flange rim for suspending the sleeve at the surface of the bone. The sleeve may also have a conical shape to facilitate advancing the sleeve into and contacting it with the bone.

The invention provides a method for securing a suture to a bone. The bone is pierced and a suture is passed through the bone. Suture ends are passed through at least two channels in the bone eyelet and the bone eyelet is placed in the opening in the bone. The suture ends are then tied, thus securing the suture to the bone. The bone may be pierced with a drill or with a driver as described above. The suture may be connected directly to a tissue or to a medical device, such as a sling, a quick connect device, a suture button, a staple, an implant, or to itself. Appropriate tension on the suture may be provided, for example with use of a suture tensioner.

The invention also provides a quick-connect bone suture fastener for fastening suture to a bone. The suture fastener consists of a sleeve and a sleeve plug. The sleeve has at least two openings through which suture may pass. The sleeve is adapted for inserting into a bone, and has a surface for frictionally contacting the sleeve plug, which functions to occlude at least one of the openings. The friction surface of the sleeve may be threaded for contacting with a threaded sleeve plug; the friction surface also may be a plurality of flanges that overlie the top of the sleeve plug after the plug is inserted into the sleeve. There also may be a friction surface on the outside of the sleeve for contacting with the bone. The sleeve may have a flange rim for suspending the sleeve at the surface of the bone. The sleeve may also have a conical shape to facilitate advancing it into and contacting it with the bone.

This aspect of the invention provides a method for quick connection of a suture to a bone. A bone is pierced and a suture is passed through the bone and through the sleeve. The sleeve is then pressed into the opening in the bone. The sleeve plug is then inserted into the sleeve, and the suture is secured. The bone may be pierced by drilling or by driving a guide through the bone. The suture may be attached to tissue or to a device, as described above. The suture may be tensioned with a suture tensioner prior to placement of the sleeve plug.

BRIEF DESCRIPTION OF THE DRAWINGS

FIG. 2b illustrates the insertion of a dilator into the vaginal hiatus over the needle of FIG. 2a.

FIG. 9a is a transverse cross section taken along the line 9—9 in FIG. 8, showing the distal end of the first jaw of the driver in position in the vagina, with cannulas forming a passage through the pubic bone and into the vagina.

FIG. 9b is a cross section as in FIG. 9a that illustrates passage through the cannulas of a suture and connecting device.

FIG. 10a is a cross section as in FIG. 9a, showing the pubic bone, the urethra, the hiatal region and the vagina, with sutures attached on the right and left sides of the upper vaginal wall.

FIG. 10b is a cross section as in FIG. 10a, showing elevation of the urethra resulting from tensioning of the sutures.

DETAILED DESCRIPTION OF THE PREFERRED EMBODIMENTS

The treatment of incontinence for intrinsic sphincter deficiency (ISD) can often be corrected surgically with the placement of a sling. This sling may consist of a wide variety of well known biocompatible materials: bovine pericardium, autograft, synthetics, cadaveric tissue, collagen/synthetic blends and the like. The sling also may be placed through a variety of surgical procedures. Slings suitable for use in urethral or bladder neck stabilization or suspension procedures and methods for implanting them are disclosed in the copending U.S. Patent Application entitled "Stabilization Sling for Use in Minimally Invasive Pelvic Surgery" U.S. patent application Ser. No. 09/023,398, filed simultaneously herewith, and the identically titled U.S. Provisional Patent Application Ser. No. 60/038,379, filed Feb. 13, 1997, the disclosures of which are incorporated herein by reference. The extent of surgical intervention is a surgeon's preference, but all present surgical interventions require a vaginal incision. The presence of microorganisms is high in the vagina; in procedures utilizing slings of non-autologous material, a high rate of infection has been reported. The procedure described herein approaches sling placement in a different manner from that requiring a vaginal incision. The vaginal hiatus is approached just under the distal urethra and a cavity is dilated within the tissue parallel to the urethra and upper vaginal wall. This device and resultant pocket provide access for placement of the sling in the treatment of ISD and urethral hypermobility. The dilator also may be used in an approach from within the vagina to create a pocket in the desired location approaching the bladder neck.

Figure 1:
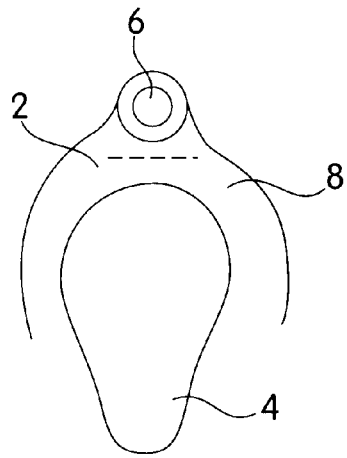
FIG. 1 shows the urethra, the vaginal wall and the vagina in transverse cross section.

Turning now to the drawings, FIG. 1 shows the urethra and the vagina 4 with the vaginal wall 8 in between. The dotted line in FIG. 1 represents an incision site in the vaginal hiatus 2. The vaginal hiatus 2 is the external tissue between the urethra and the vagina 4, as well as the tissue deep to that external tissue. The vaginal wall 8 is intended to refer to all interior surfaces of the vagina 4.

The series of FIGS. from 2a to 2g demonstrates a sequence having to do with one aspect of the present invention, referred to herein as the dilator 10. The dilator 10 consists of two distinct functional units, the insertion spreader 12 and the handle 18. The insertion spreader 12 can have the appearance of a split tube, and each half of the insertion spreader 12, or each half of the split tube, can be an elongated semi-cylindrical spreader guide 14. The invention contemplates spreader guides 14 shaped other than semi-cylindrically, such as spreader guides 14 whose cross section when joined would describe a square, a hexagon, and the like, depending on the application for which it is used, and depending on the configuration of the card, to be discussed below.

Figure 2A:
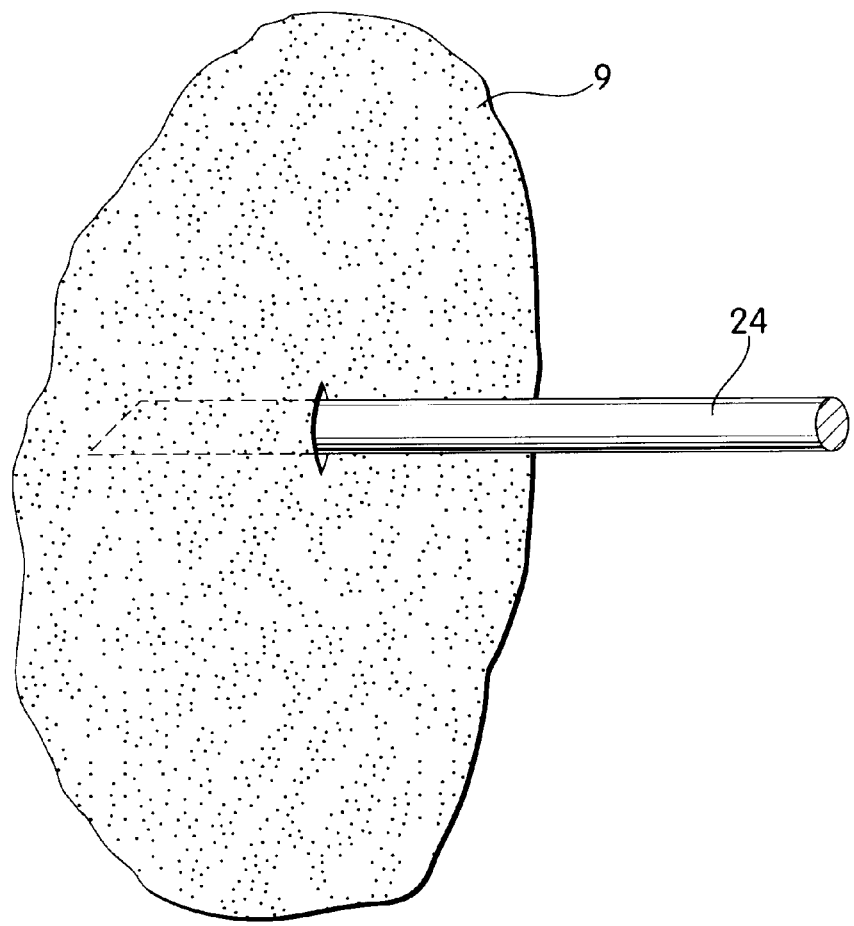
FIG. 2a represents the insertion of a needle into the vaginal hiatus.
Figure 2B:
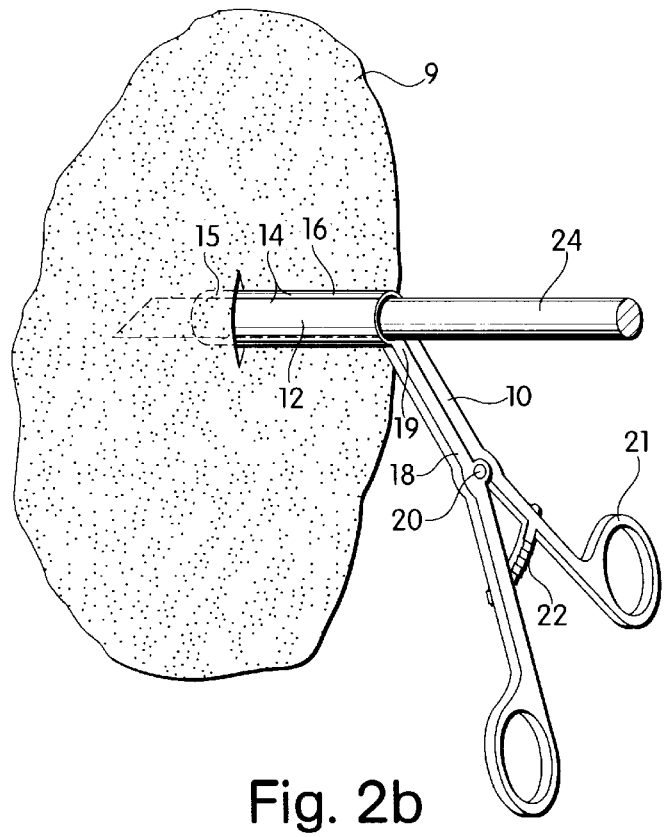
Figure 2C:
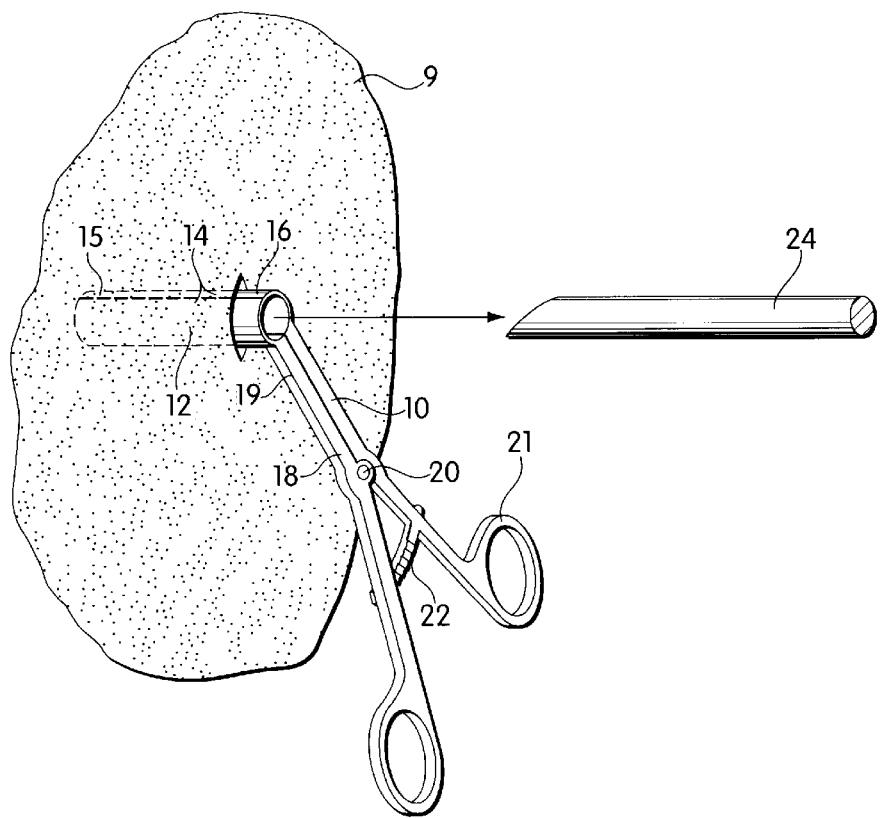
FIG. 2c depicts the withdrawal of the needle of FIG. 2a and further insertion of the dilator of FIG. 2b.
Figure 2D:
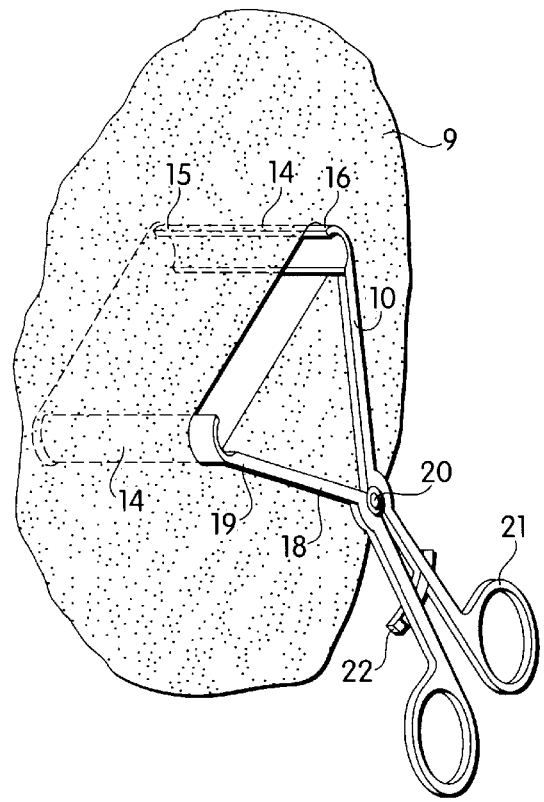
FIG. 2d represents the dilator of FIG. 2c in the open position.

The spreader 12 has an open position in which the spreader guides 14 are separated from each other, as in FIG. 2d, as well as a closed position in which the spreader guides 14 are closely aligned, substantially forming a cylinder, as in FIG. 2c. The preferred separation of the spreader guides 14 in the open position is approximately 2.5 to 4 cm.

The spreader guides 14 are substantially parallel to each other whether the spreader 12 is in the open or closed position, or is moving from one position to another. The spreader guides 14 have a distal end 15 and a proximal end 16, the distal end 15 being for insertion into the tissue 9, and the proximal end 16 being for attachment to the handles 18. In a preferred embodiment of this invention, the spreader guides 14 are sharpened at the distal end 15, to facilitate entry into a tissue 9 and passage therethrough. The distal ends 15 of the spreader guides 14 also may be shaped to cooperate with a needle 24, which may be inserted first into the tissue 9 (see FIG. 2a) before insertion of the spreader guides 14, to provide a path for the spreader guides 14 to follow into the tissue 9 as they are inserted over the needle 24 (FIG. 2b).

The handles 18 of the dilator 10 have first 19 and second 21 ends. The first end 19 of each handle 18 is connected to the proximal end 16 of each guide. The second end 21 of each handle 18 is adapted for a physician to grasp and manipulate the handles 18. The handles 18 are joined at a pivot 20 and may be moved about the pivot 20 relative to one another, in such a way that movement of the handles 18 translates to displacement of the spreader guides 14 relative to one another. In a preferred embodiment of the invention, a ratcheting lock 22 is also part of the handles 18, and provides a mechanism for the handles 18 to be locked into a particular position, thus also locking the spreader 12 in a particular position.

This aspect of the invention provides a method for creating a cavity in a tissue 9. The needle 24 is optionally first inserted into the tissue 9 as in FIG. 2a. The spreader guides 14 of the spreader 12 are placed in a closed position and are inserted into the tissue 9 over the needle 24 (FIG. 2b) or directly into the tissue 9. The needle 24, is used, is then withdrawn (FIG. 2c). When the spreader guides 14 are inserted to the desired depth, the handles 18 of the dilator 10 are moved together, as shown in FIG. 2d. This causes a separation of the spreader guides 14 until the dilator 10 is in the open position. The movement of the spreader guides 14 away from each other toward the open position creates a cavity in the tissue 9.

In a preferred embodiment of the method of this invention, the tissue 9 is the vaginal hiatus 2. In some cases, the practice of this method may be facilitated with the additional step of preforming an episiotomy on the skin of the vaginal hiatus 2. In an alternative embodiment, this method may be practiced on a tissue 9 of the vaginal wall 8, for example the upper vaginal wall, to create a cavity between the vagina 4 and the urethra. Also contemplated in this invention is the practice of this method in any tissue 9 wherein it may be advantageous to simultaneously create a cavity and provide guide tracks for placement of a medical device within the cavity.

An additional preferred embodiment of the method of the invention has as a first step the insertion of a needle 24 into the target tissue 9, such as the vaginal hiatus 2 or vaginal wall 8, as in FIG. 2a. The needle 24 may be calibrated or otherwise marked to indicate the depth of its insertion, to allow a physician to accurately determine the proximity of the tip of the needle 24 to an internal structure, such as the bladder neck 47. In addition to a determination of the depth of penetration, the needle 24 may also provide a path for simplified insertion of the spreader 12 of the invention.

Using an embodiment of the dilator 10 wherein the distal ends 15 of the guides 14 are adapted for cooperating with a needle 24, the spreader 12 is moved to the open position, and the spreader 12 spreader guides 14 are placed near the needle 24, then the spreader 12 is moved to the closed position. In the closed position the spreader guides 14, at least at their distal ends 15, substantially conform to the shape of the needle 24 and may follow its path into the tissue 9, as in FIG. 2b. The spreader guide 14 is then inserted to the desired depth, at which point the needle 24 may be withdrawn, as in FIG. 2c. Then, as before, the handles 18 are moved closer together, thus moving the spreader guides 14 away from each other to the open position (FIG. 2d). The ratcheting lock 22 portion of the handles 18 holds the handles 18 together and the spreader guides 14 apart. Movement of the spreader guides 14 to the open position creates the cavity desired for insertion of a medical device, or for performing a desired surgical procedure.

As an alternative embodiment of this method, an additional step may be preformed to facilitate creation of the cavity. In this embodiment, the target tissue 9 is fluid-dissected by injecting a solution into the tissue 9 prior to advancing the insertion spreader 12 into the tissue 9. This additional step of hydro-dissection may be preformed using a variety of physiologically suitable buffers or solutions. This additional step provides an advantage in some cases, because hydro-dissection may be tissue-selective with respect to the vaginal hiatus 2 and the urethra. That is, hydro-dissection may tend to preferentially dissect hiatal tissue without impinging upon urethral or bladder tissue. Accordingly, a first step of hydro-dissection that creates a saline bolus, may predissect the tissue without affecting the integrity of the urethra. The subsequent step of passing the insertion spreader 12 into the tissue is therefore simplified, and the movement of the spreader guides 14 into the open position is also simplified, because a substantial portion of the cavity is already created by the process of hydro-dissection.

In one method of hydro-dissection and subsequent cavity opening with use of the dilator 10, a needle is inserted into the upper vaginal wall 8 and the saline solution is delivered into the deep tissue of the vaginal hiatus 2. The deep tissue of the vaginal hiatus 2 is thereby dissected by the injected solution. Subsequent insertion of the spreader 12 through the external skin of the vaginal hiatus 2 provides a route of entry that is less susceptible of infection than may be the case where a tissue cavity is created entirely transvaginally. Because the interior of the vagina 4 harbors more microorganisms than the surface of the vaginal hiatus 2, and is also much more difficult to surface sterilize, the exterior vaginal hiatus 2 may often be the preferred route of entry for creating a tissue cavity for urethral and pelvic floor reconstruction. However, certain circumstances may dictate creation of a tissue cavity transvaginally; the dilator 10 of the invention and the methods of its use are fully adaptable to creation of a cavity transvaginally. Thus, the present invention provides a surgeon with a convenient means of opening a tissue cavity and with alternative avenues of entry to the tissue cavity. Additional devices and methods for transvaginal urethral or pelvic floor reconstruction and urethral or bladder neck stabilization or suspension, suitable for use in connection with the present invention, are disclosed in the copending U.S. patent application Ser. No. 08/744,439 entitled "Transvaginal Anchor Implantation Device," filed on Nov. 8, 1996, the disclosure of which is incorporated herein by reference.

Figure 2E:
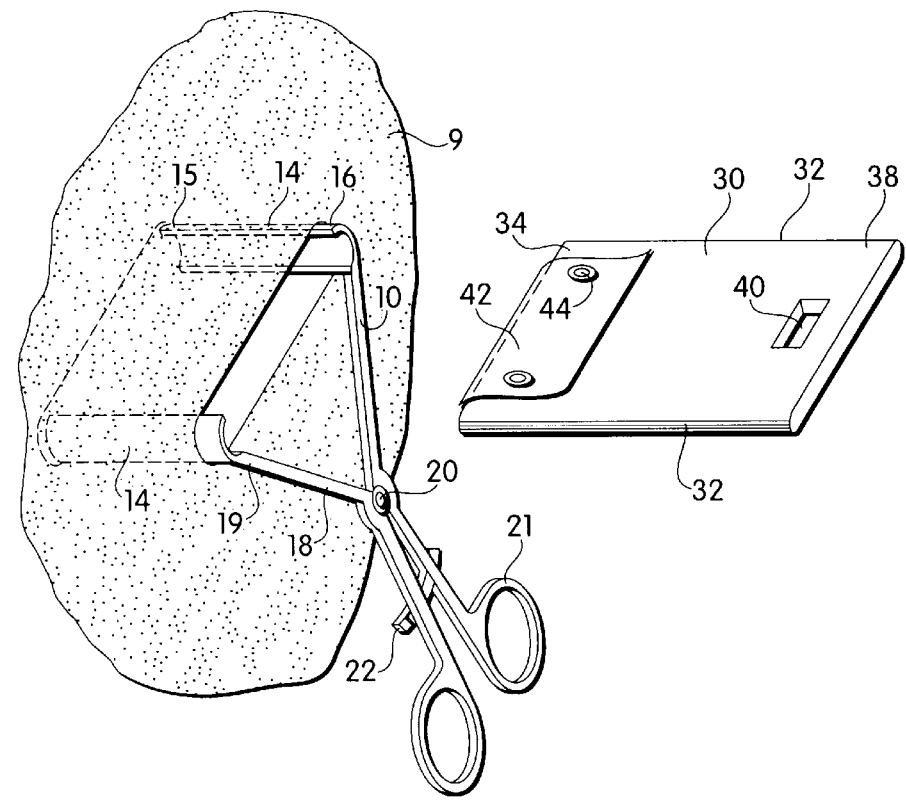
FIG. 2e illustrates the alignment of the insert card with the guides of the dilator of FIG. 2d.

Another aspect of the present invention is a card 30 for advancing a medical device into a tissue cavity as shown in FIG. 2e. The card 30 has lateral edges 32, a distal portion 34, and a proximal portion 38. A part of the proximal portion 38, the articulation opening 40, may be adapted for articulation with additional devices that may be useful in positioning or stabilizing the card 30 in certain methods of use. The distal portion 34 of the card 30 is adapted for carrying a medical device into a tissue cavity. In one embodiment of the invention the medical device is a urethral sling 42 in one embodiment the sling 42 includes one or more ring members 44. The card 30 enables sling 42 manipulation without touching the sling 42. This reduces contamination, and establishes the sling 42 position within the body and relative to other devices that may be used in positioning and securing the sling 42. The lateral edges 32 of the insert card 30 may be specially adapted to articulate with spreader guides 14 that provide a path into the tissue cavity, such as the spreader guides 14 of dilator 10. The distal portion 34 of the card 30 is inserted into the cavity by aligning it with the proximal ends 16 of the spreader guides 14. Once the card 30 is thus aligned, the edges 32 of the card 30 easily slide along the semi-cylindrical spreader guides 14 into the cavity until reaching the proper depth in the cavity.

The card 30 and dilator 10 of the invention thus may be used in a method for inserting a medical device into a tissue cavity. In a preferred embodiment of this invention, the medical device is a sling 42. Other medical devices that may be positioned with use of the card 30 include pharmaceutical implants, therapeutic devices, closures, staples and clips. In the preferred method, a urethral sling 42 is placed at the distal region of the insert card 30. A cavity is formed in a target tissue 9 as described above. Briefly, the spreader 12 is placed in a closed position and the spreader guides 14 are positioned against the surface of the target tissue 9. The spreader 12 is inserted into the target tissue 9 and is then moved to the open position by moving the handles 18 of the dilator 10 together. The spreader 12 is held in the open position by the ratcheting lock 22. With the sling 42 on the card 30 and the cavity opened, the card edges 32 are aligned with the semi-cylindrical spreader guides 14 of the dilator 10 and the card 30 is inserted into the cavity until it reaches the desired depth. The card 30 is manipulated by its proximal portion 38, and may be manipulated by means of an accessory tool contacting the card 30 at the articulation opening 40.

There are several advantages to this method of the invention. One advantage is that the medical device can be placed without excessive contact between the device and the patient. Excessive contact between the surgeon and the device also may be avoided, which allows a reduction in handling and a reduced likelihood of contamination. This fact minimizes the risk of infection in the placement of the device. Another advantage is that the card 30 provides support for the device in subsequent steps of attaching the device in place inside the tissue cavity. A further advantage is that the spreader guides 14 provide tracks along which the card 30 may enter, minimizing difficulties and variability in the location of the sling 42 in the desired position.

This method is applicable to cavities made in the vaginal hiatus 2 as well as in the vaginal wall 8, specifically in the upper vaginal wall. Other uses for this method, involving the placement of a medical device supported on a card 30 with the assistance of the dilator 10 of the invention, will be evident to those of skill in the art.

Figure 2F:
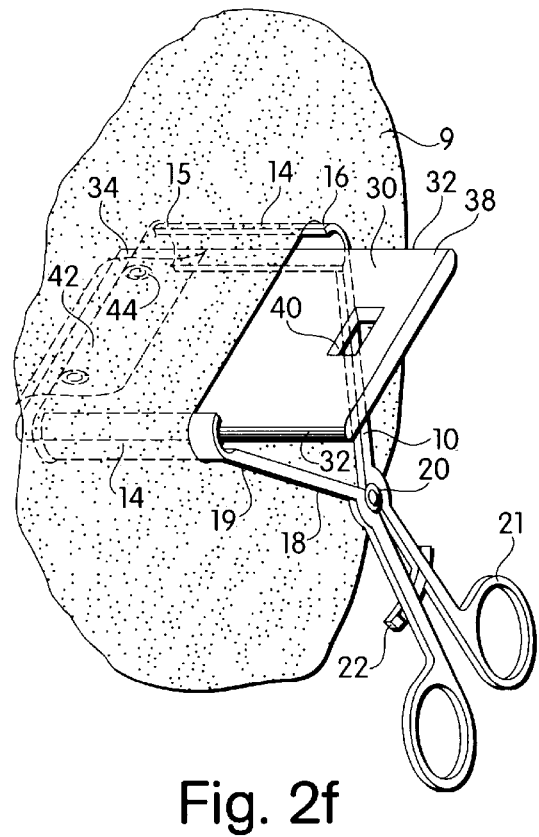
FIG. 2f shows the insertion of the insert card between the guides of the dilator of FIG. 2d.
Figure 2G:
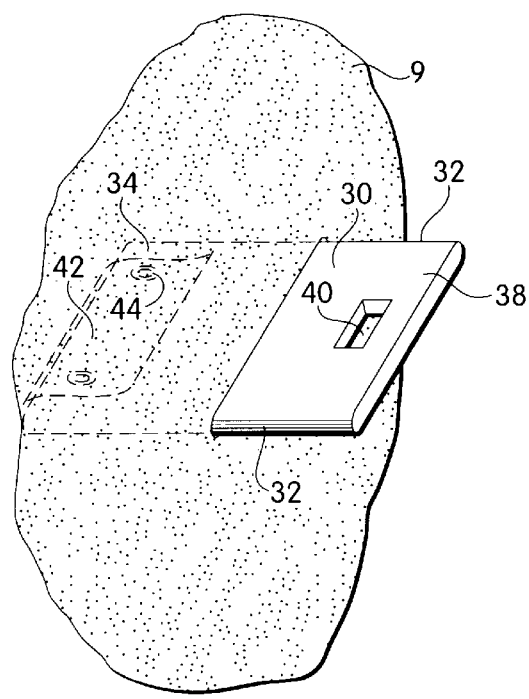
FIG. 2g shows the insert card in position in the hiatus after withdrawal of the dilator.

FIGS. 2e, 2f and 2g show the steps of the method after the cavity is created. In FIG. 2e the card 30 holding the sling 42 is aligned with the spreader guides 14 of the dilator 10. In FIG. 2f the card 30 is inserted into the cavity by sliding the sides of the card 30 along the semicircular tracks provided by the spreader guides 14 of the dilator 10. FIG. 2g shows the card 30 in position in the tissue cavity after removal of the dilator 10. As can been seen in FIG. 2g the proximal portion 38 of the card 30 and the articulation opening 40 remain outside the cavity for continuing or subsequent interaction with accessory tools, such as those which are disclosed below in a discussion of other aspects of this invention.

The placement of the sling 42 or some other medical device by the method of this aspect of the invention preferably precedes the securing of such a medical device inside the tissue cavity. The invention contemplates securing the sling 42 or other medical device in several different ways. In one embodiment the sling 42 may be placed in the cavity to be sutured therein by a suture 88 entering the cavity from the upper vaginal wall 8. In another embodiment the sling 42 may be stapled or anchored into place subsequent to its positioning with the use of the card 30. Suturing of the sling 42 into position also may be accomplished percutaneously, or with the suture being advanced from above or through the bone. Additional devices and methods for percutaneous and hiatal approaches for urethral or pelvic floor reconstruction and urethral or bladder neck stabilization or stabilization, suitable for use in connection with the present invention, are disclosed in the copending U.S. Patent Application entitled "Percutaneous and Hiatal Devices and Methods for use in Minimally Invasive Pelvic Surgery" U.S. patent application Ser. No. 09/023,965, filed simultaneously herewith, and the identically titled U.S. Provisional Patent Application Ser. No. 60/038,171, filed Feb. 13, 1997, the disclosures of which are incorporated herein by reference.

Preferred methods of securing the sling 42 in place may involve anchoring the sling 42 to a bone via a suture 88 and a bone anchor, or may involve attaching the sling 42 to a suture 88 which passes through a bone, such as the pubic bone. This preferred embodiment of the method of attaching the sling 42 into place after it has been delivered into a tissue cavity by the card 30 of the invention will be discussed below in connection with other aspects of the present invention. It will be evident to those of ordinary skill in that art that the method of this aspect of the invention will be applicable to the positioning of several kinds of medical devices. Such medical devices may be secured into place after their positioning by one of several known techniques.

Another aspect of the invention provides an incision guide 50 (see FIG. 5) for cutting a cavity between the urethra and the vagina 4, in the hiatal tissue. The incision guide 50 consists of a rigid catheter 52 and a cutter 54, and may also consist of several other accessories to enhance or vary the performance of the incision guide 50. The rigid catheter 52 is a modified Foley-type catheter, preferably having a shaft of metal or other rigid material over the surface of the catheter.

Figure 3:
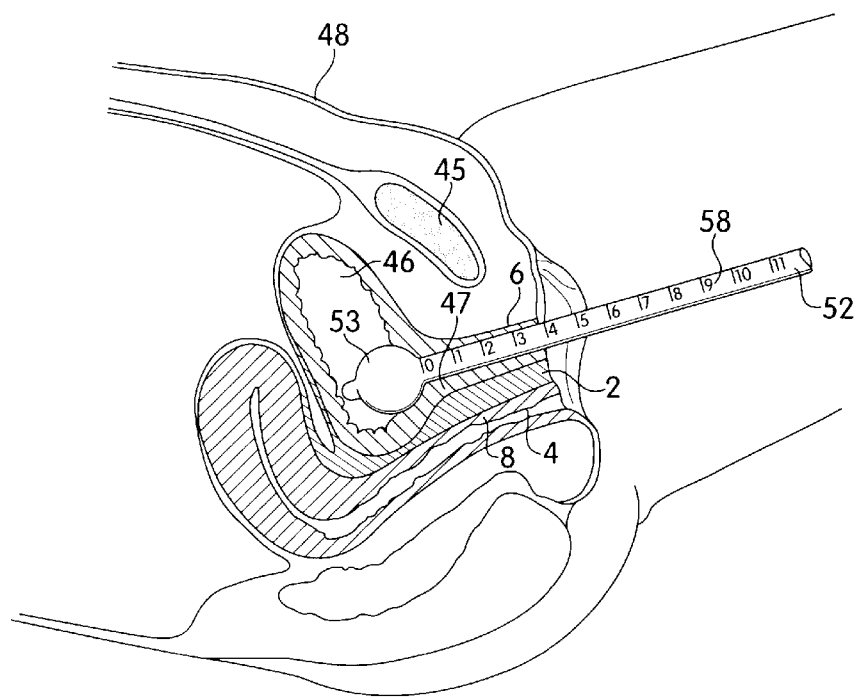
FIG. 3 is a partial longitudinal cross section of the vagina, urethra, and bladder showing a rigid catheter in place in the urethra.

The catheter 52 is inserted into the urethra and an integral bladder neck balloon 53 is inflated. (FIG. 3.) The rigid catheter 52 straightens the urethra and extends externally to provide a guide for attachment of devices which advance parallel to the urethra along the central hiatus plane. The balloon 53 holds the catheter 52 in place. Such devices which track along the rigid catheter 52 are used for dissecting the hiatus 2 laterally between the urethra and the upper vaginal wall 8 from the proximal urethra. A number of different methods are contemplated.

The catheter 52 is therefore insertable into the urethra and is adapted for indicating the position of the bladder neck 47. The rigid catheter 52 functions to expand and straighten the urethra, providing a fixed reference point in the soft tissue of the urethral floor and hiatal plane. This fixed reference function also facilitates a surgeon's determination of the lateral position of the urethra by palpation, or with any of several forms of instrumentation.

Figure 4:
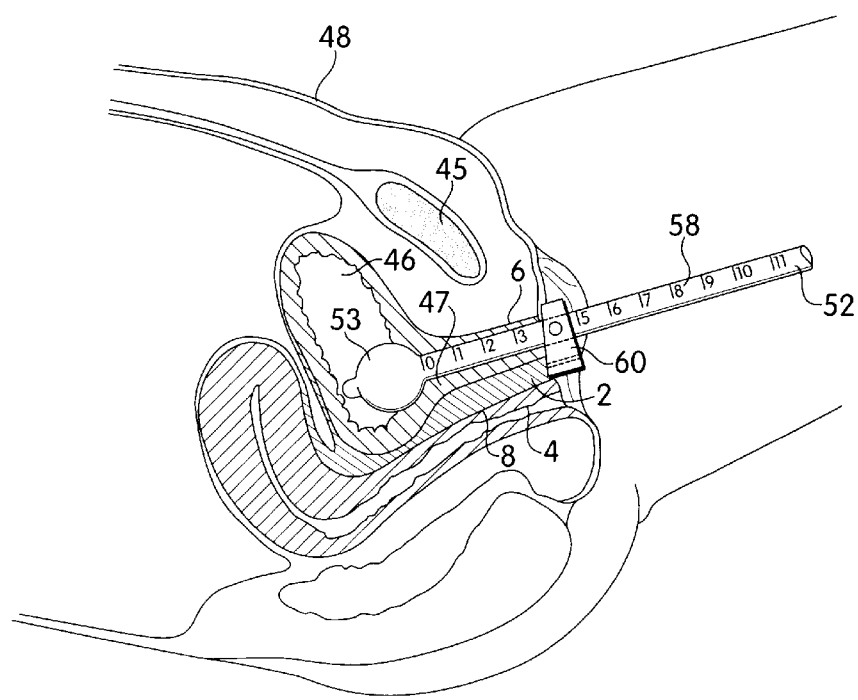
FIG. 4 is a cross section as in FIG. 3, and shows a rigid catheter with the stop attached.
Figure 5:
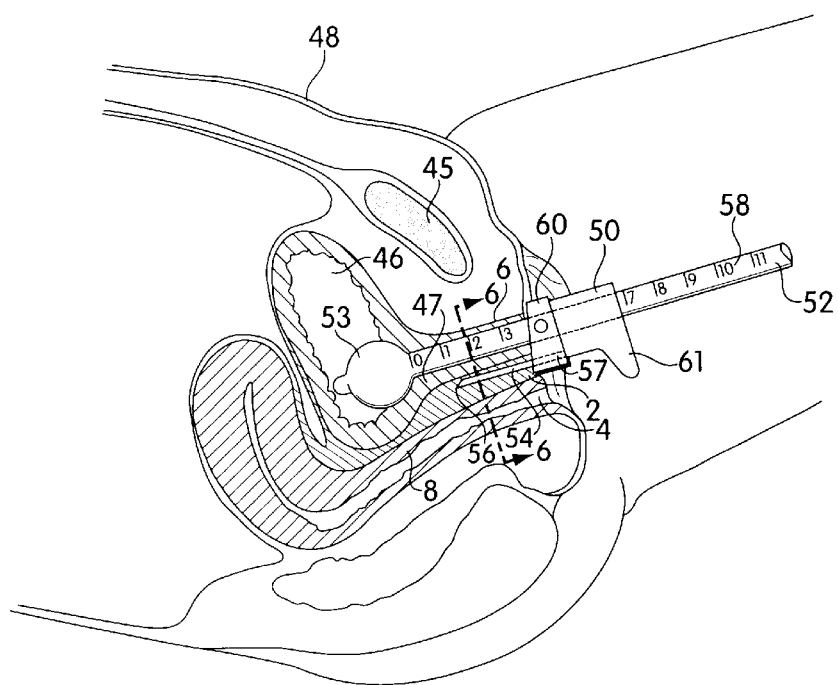
FIG. 5 is a cross section as in FIG. 3, and shows an incision guide assembly with a catheter, stop, and cutter in place.

The catheter 52 is designed to be of sufficient length to reach to the bladder 46 and also to extend outside the body of the patient. The catheter 52 will preferably have graduation marks or other indicia 58 thereon to indicate the distance from the surface of the distal urethra to the bladder neck 47 and the bladder 46. (FIG. 4.) The catheter 52, therefore, as it runs from the bladder neck 47 to the distal urethra and beyond, provides access for mounting and guidance of other devices, such as the cutter 54. (FIG. 5.)

The cutter 54 is used for forming the desired cavity at a position that is a fixed distance from, and therefore parallel to, the urethra. The cutter 54 has a longitudinal axis of similar dimensions to the catheter 52, and has a cutting end 56 and a connecting end 57. The cutter 54 is adjustable at its connecting end 57 with the exterior portion of the rigid catheter 52 and can slide along the catheter 52, thus providing tracking guidance for the cutter 54. (FIG. 5.)

The manner of attachment between the cutter 54 and catheter 52 will determine the amount of offset between the cavity and the urethra. The preferred distance of offset between the cutter 54 and the catheter 52 is approximately 0.5 cm. This distance would in most patients position the cutter 54 to roughly bisect the distance between the upper vaginal wall 8 and the urethra. Because of the variability in the anatomy of patients, and the other ways in which this approach can be applied, a preferred range of offset may be from 0.25 cm to 0.75 cm. In other embodiments a useful range may be from 0.1 cm to 0.9 cm. Again, because of the variability in patient anatomy, in some cases it may be advantageous to further offset the cutter 54 from the catheter 52 by a distance of 1 cm or more.

Figure 6A:
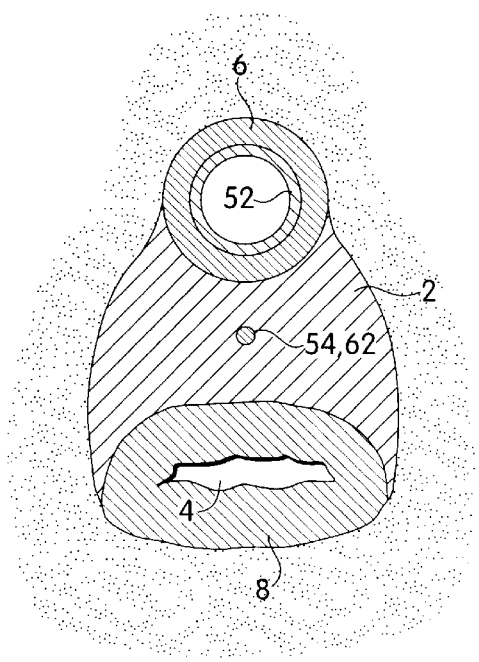
FIG. 6a is a transverse cross section taken along the line 6—6 in FIG. 5 and illustrates the hiatal region of the patient with the catheter in place and the cutter as a needle.
Figure 6B:
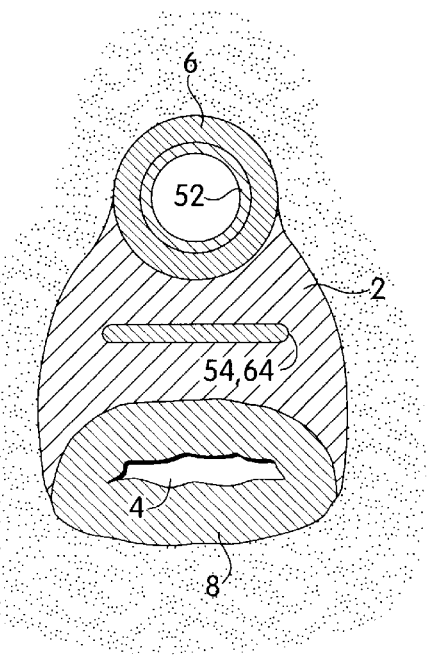
FIG. 6b is a transverse cross section as in FIG. 6a and shows the hiatal region with the catheter in place and the cutter as a blade.

The cutter 54, being adapted to articulate with and slide along the axis of the catheter 52, provides a means for creating a cavity in the vaginal hiatus 2. This cavity is in a predictable and optimally safe plane between the urethra and the upper vaginal wall 8. The desired dimensions of the cavity may vary widely depending on the anatomy of the patient and the purpose for which the cavity is made. In some cases, a preferred cutter 54 for attachment to the catheter 52 is a needle 62. (FIG. 6a.) In other cases a preferred cutter 54 is a blade 64. (FIG. 6b.)

A third preferred cutter 54 is a bipolar knife, providing lateral dissection of the vaginal hiatus 2 that is bloodless, by cutting and coagulating the tissue simultaneously. With use of the bipolar knife, it is preferable to equip the metal portion of the catheter 52 with thermistors along its length, to measure the heat generated by the bipolar knife and provide temperature information to the surgeon. One embodiment of the bipolar knife, also known as the bipolar cutting loop, consists of a pair of wires, one flexible and one rigid, through which a current is passed to heat the loop.

Preferred dimensions of the cavity that is created may be from 1 to 3.5 cm deep and may have a width ranging from the width of a needle 62 to approximately 3.5 cm. The most preferred width for applications in which a sling 42 is to be installed is approximately 2 to 4 cm. The preferred depth of penetration of the cutter 54 is, of course, a function of the particular anatomy of a given patient, and is to be determined by the surgeon after insertion of the rigid catheter 52 and reference to the indicia 58 thereon.

Modified embodiments of the incision guide 50 include the attachment of various other devices to further optimize the control that a surgeon may exercise over the depth and direction of penetration of the cutter 54 device. One such modification is to add one or more stops 60 to the device, as shown in FIG. 5. In one embodiment of this modification, one stop 60 is movably and lockably positioned on the catheter 52. This stop 60 may have the form of a ring or a block, and may be locked at a particular position of the catheter 52 by means of a thumb screw or a spring snap that articulates with the indicia 58 on the catheter 52 at various positions along its length. The stop 60 slides onto the end of the end of the catheter 52 and may be locked in a certain position on the catheter 52 to prevent advancement of the cutter 54 past the position of the stop 60. The cutter 54 may also have a block 61 intended to abut the stop 60 that is placed on the catheter 52. Therefore the cutter 54 which slides along the catheter 52 may attach by means of a stop block 61, or by other means of attachment that may similarly function as a stop block 61.

This aspect of the invention provides a method for creating a cavity in the vaginal hiatus 2. The method begins with insertion into the urethra of the rigid catheter 52. (FIG. 3.) The preferred catheter 52 is, as discussed above, provided with indicia 58 to indicate the position of the bladder neck 47. The catheter 52 extends from the distal urethra of the patient, providing a linear guide for the cutter 54. According to the method, the position of the bladder neck 47 is determined. Next the cutter 54 is positioned on the catheter 52 and is advanced toward the patient along the catheter 52 until the cutter 54 contacts and penetrates the vaginal hiatus 2. (FIG. 5.) The cutter 54 is then inserted into the vaginal hiatus 2 to a predetermined depth, thus creating a cavity in the vaginal hiatus 2 that does not extend to the bladder neck 47.

This method allows a surgeon to make an incision into the vaginal hiatus 2 in a way that optimizes the safety, reproducibility, and reliability of the procedure. With a preferred embodiment of the incision guide 50 as discussed above, the depth of insertion may be very precisely controlled, preventing damage to the bladder neck 47. Likewise, the displacement between the urethra and cutter 54 is maintained constant, thus assuring that creating the cavity will not compromise the urethra or the vaginal wall 8.

The various embodiments of the incision guide 50 also provide precise control of the width of the incision. For example the incision width may be that of a needle 62 (FIG. 6*a*) of a selected gauge, or it may be the width of a selected blade 64 (FIG. 6*b*), or it may be the width determined by the dimensions and orientation of the wires in a bipolar knife. An additional benefit of the method of the invention is that, because the cutter 54 tracks along the rigid catheter 52, and therefore tracks along the urethra itself, there is a constant lateral relationship between the dimensions of the pocket and the position of the urethra. This assures that the cavity will have the dimensions, orientation, and position to optimize placement of a device within the cavity.

The depth of incision and the distance of offset between the urethra and the cavity thus created is determined by the dimensions of the attachment block 61 between the cutter 54 and the rigid catheter 52. (FIG. 5.) In a preferred embodiment of the invention, wherein the rigid catheter 52 has attached thereto a stop 60, the stop 60 may be precisely positioned to prevent the advancing of the cutter 54 to a depth that would create a risk of damaging structures of the bladder 46.

Where the rigid catheter 52 is also equipped with thermistors, providing temperature feedback for safe use of the bipolar knife, an incision may be made rapidly and bloodlessly. Because of the potential damage caused by a bipolar knife in tissue close to critical structures such as the bladder 46 and urethra, many physicians would ordinarily hesitate to make incisions with such an instrument. However, this concern is addressed through the use of the present method because the orientation of the cutter 54 and the catheter 52 provides very precise control over the offset between the cutter 54 and the catheter 52 as well as over the depth of penetration of the cutter 54.

The incision guide 50 may be combined with the insert card 30 to provide a method for inserting a medical device into a cavity. In this method a tissue cavity is created according to the steps of the method provided immediately above, and a card 30 supporting a medical device is inserted into the cavity. The medical device may be a pharmacologically active implant, a prosthetic balloon, or a therapeutic device. In a preferred embodiment of this method, the medical device is a urethral sling 42, as in FIG. 2*e*. After the cavity is created with use of the incision guide 50, the card 30 may be inserted directly into the cavity, depending on the dimensions of the card 30 and the cavity. The medical device may be secured within the cavity by a variety of means, after which the card 30 may be withdrawn. Alternatively the card 30 may be withdrawn before the device is secured.

An additional embodiment of the method of the invention combines use of the dilator 10 of the invention together with the incision guide 50 and the card 30. A cavity is created with use of the incision guide 50, as explained above, and then the cavity is stabilized and further defined by insertion of the spreader 12, which is then moved to the open position, as in FIG. 2*d*. With the spreader 12 in the open position, the cavity may be stretched, if necessary. The cavity is also provided with tracks along which the card 30 may easily slide to enter the cavity, as in FIGS. 2*e* and 2*f*. Thus, the invention contemplates the use of the devices of the invention alone or in combination, in order to achieve the desired result.

With reference to FIGS. 7, 8, 9 and 10 in another aspect, the present invention provides a driver 70 for driving a bone-piercing guide 84 through the pubic bone. Originally, passing a suture through the pubic bone was done by drilling a hole through the generally anterior portion of the pubic bone using a drill guide attached to a stabilizer and vaginal retractor device. A suture was then passed through the drilled hole with a suture passer. The present invention does not require the use of a drill and is capable of creating small passages through the pubic bone, sufficient to allow passage of a suture through the bone. The pubic bone is particularly well suited for this adaptation because it is relatively easily pierced, due to its low density.

Figure 7:
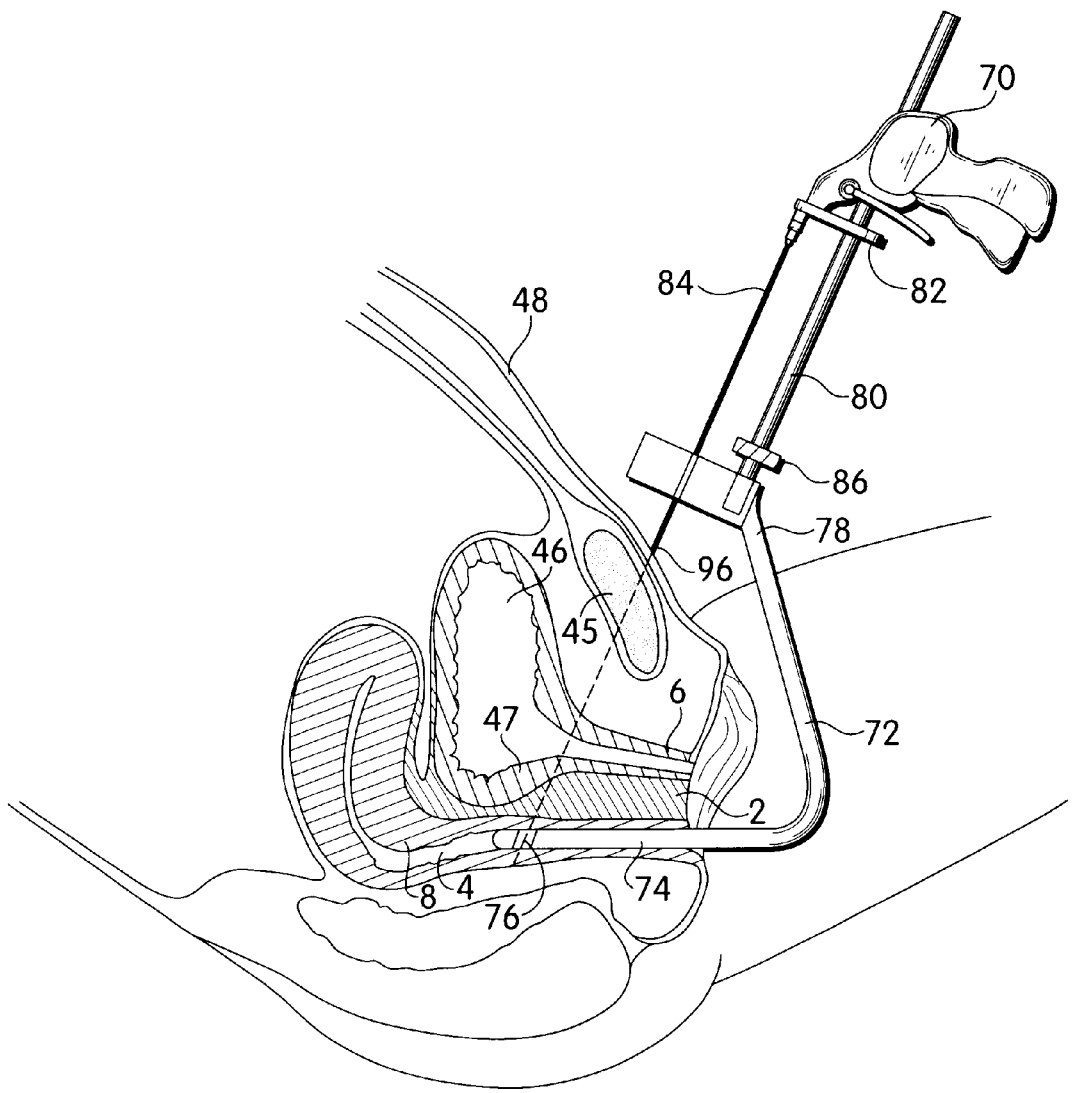
FIG. 7 is a cross section view of the pelvis as in FIG. 3 with the driver positioned above the pubic bone.

The driver 70 of the invention may be described as having four basic parts: a first jaw 72, a slide bar 80, a second jaw 82, and a bone-piercing guide 84. (FIG. 7.) The first jaw 72 has a distal end 74 and a proximal end 78. The distal end 74 is adapted for inserting into a tissue cavity and the proximal end 78 of the first jaw 72 is attached to the slide bar 80. The slide bar 80 connects the first or fixed jaw 72 with the second or moveable jaw 82. The second jaw 82 slides along the slide bar 80, with a releasable ratcheting action, toward the first jaw 72. The bone-piercing guide 84 attaches to the second jaw 82, and advances toward the first jaw 72 as the second jaw 82 is ratcheted along the slide bar 80.

Figure 8:
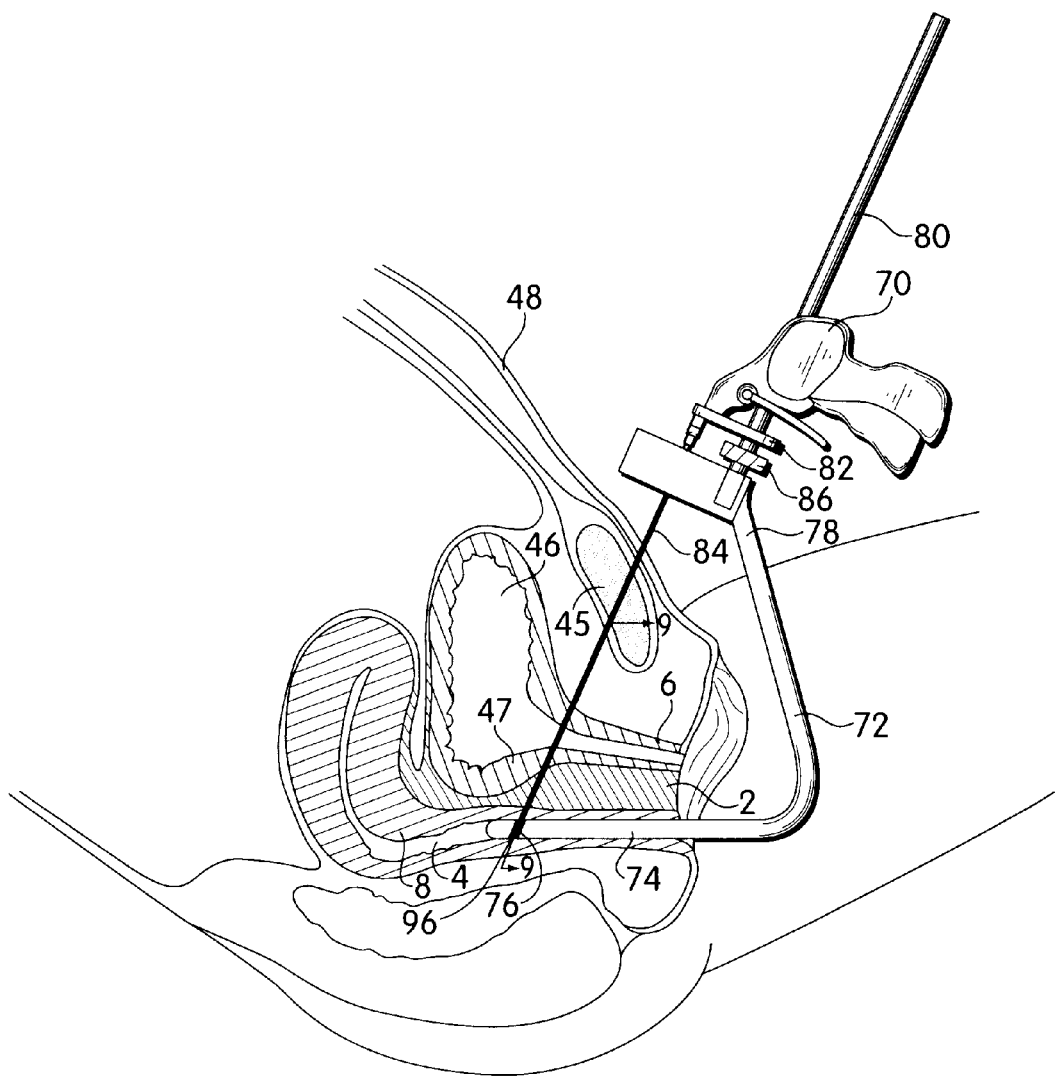
FIG. 8 is a cross section including a driver as in FIG. 7, depicting the passage of the bone-piercing guide through the pubic bone lateral to the urethra and into the vagina.

A stop 86 on the slide bar 80 prevents further closing of the jaws once the sharp end 96 of the cannula 90 exits the bone and is even with the first jaw 72. The first jaw 72 has a slot 76 so that the sharp end 96 of the cannula 90 does not actually contact it when exiting the bone. (FIG. 8.) The driver 70 may be equipped with a double cannula jaw (not shown) so that parallel passages may be created through the bone simultaneously.

Figure 24A:
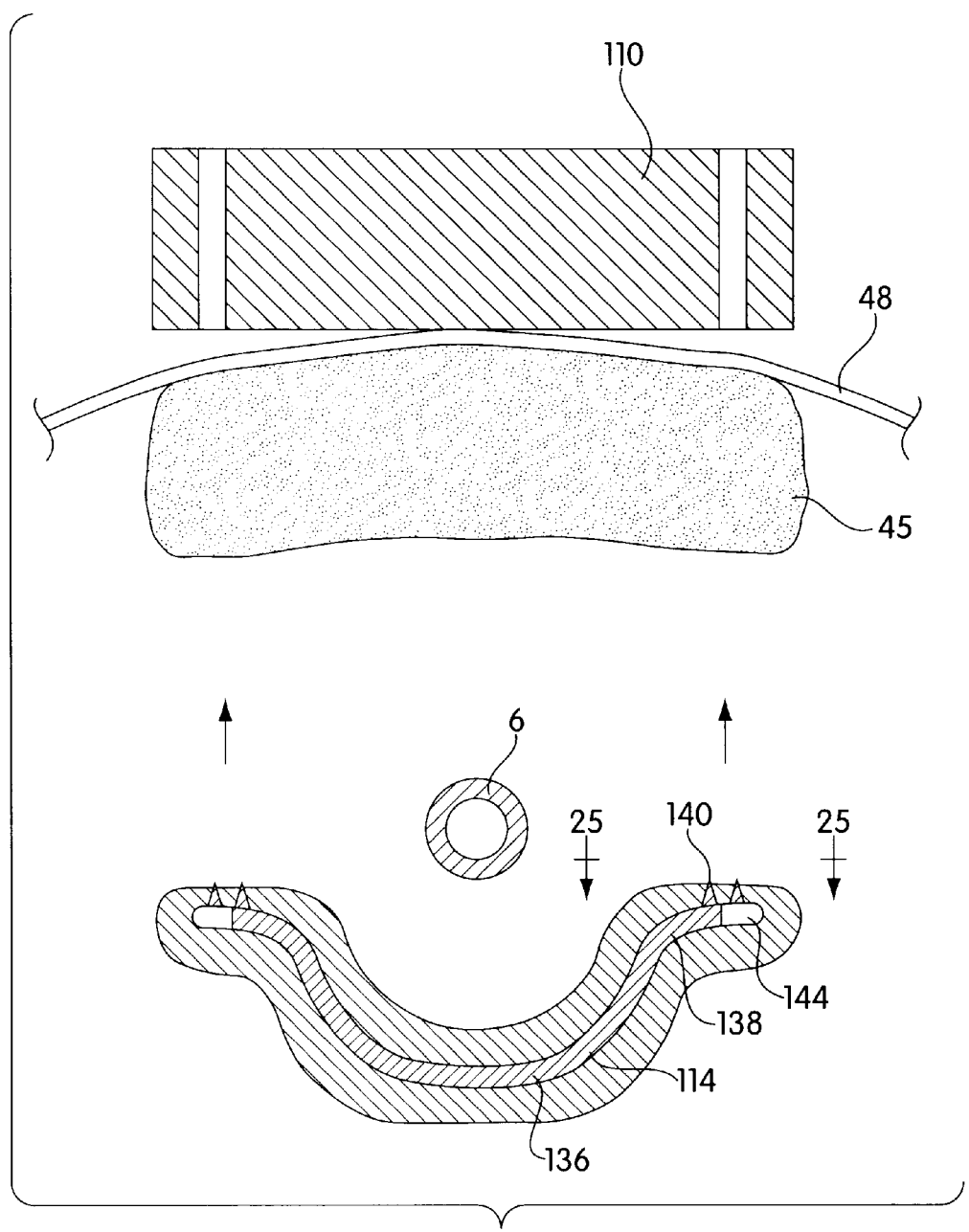
FIG. 24a illustrates in cross section the position of the concave insertion tongue with contact pins relative to the urethra, the pubic bone, and the compression foot of the driver frame assembly, prior to application of counterpressure on the pubic bone by the concave tongue.
Figure 25:
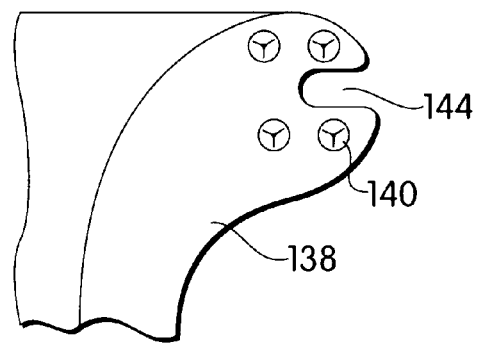
FIG. 25 is a view of the insertion tongue from the direction 25—25 of FIG. 24a, and provides detail of the elevated edge of the concave insertion tongue, showing the position of the contact pins and the passage gap.

It is the function of the first or fixed jaw 72 inside a tissue cavity to provide a counterpressure on the bone opposite the pressure applied by the bone-piercing guide 84. Accordingly, the distal end 74 of the first jaw 72 may have a shape adapted to provide positions that can appress the inferior region of the pubic bone 45 lateral to the pubic symphysis without crushing the urethra 6. Such a configuration of the distal end 74 of the first jaw 72 is shown in cross section in FIGS. 24*a* and *b*, 26*a* and *b*, and 27*a*; a detail view of a portion of the edge of the distal end 74 of the first jaw 72 is shown in FIG. 25. In these figures, the distal end 74 comprises a tongue 114 with a central depression 136 and elevated edges 138. The edges 138 may have contact pins 140 adapted for piercing the tissue lying between the pubic bone 45 and the elevated edge 138 of the tongue 114. At the elevated edge 138 there also may be a gap 144 through which a guide 84 may pass without contacting the tongue 114.

Any device with opposing jaws having one jaw adapted for insertion into a tissue cavity may preferably have a tongue configuration as described above. The choice of a desirable configuration of the distal end 74 of the first jaw 72 may be determined by one of ordinary skill in the art, taking into account anatomical considerations, the particular procedure involved, and the like.

The pubic bone is an especially important structure for piercing in surgical applications. This is true for at least two reasons: the first is that there are soft tissue structures in the proximity of the pubic bone whose dimension or displacement can result in several medical problems. The second reason is that the pubic bone is a relatively low density bone and therefore may be pierced without the application of undue force, if the force is properly oriented. The fact that the pubic bone may be pierced creates the possibility of stabilizing a soft tissue structure near the pubic bone by attaching a device or a suture to the soft tissue structure and stabilizing it by attachment to the relatively immovable pubic bone. In addition, by piercing through the bone, the suture locking and tissue securing method may be accomplished from the superior/anterior bone surface, which is much more accessible than the posterior/inferior surface. The prior need to work near or at the posterior/inferior surface of the pubic bone arose from the proximity of this surface to the structures most often sought to be stabilized. With the methods and devices of the present invention, however, passage of suture through the pubic bone combines the desired proximity to structures beneath the bone, with the convenience and simplicity of introducing and securing suture through the upper surface of the bone. Therefore the bone driver 70 of the present invention provides a device of potentially wide applicability for stabilizing structures of the pelvis, particularly in reconstruction and stabilization of the urethral and pelvic floor.

Alternative approaches to stabilizing structures of the urethral and pelvic floor or other soft structures of the pelvis by attachment to a fixed reference tissue have relied on drilling a hole into the surface of a bone and placing into the hole a bone anchor to which a suture is attached. The difference between such approaches and the present approach is that the present invention allows a much smaller opening to be made. This opening traverses the bone rather than being simply on the surface of the bone. Through this much smaller passage may be passed a suture, without the need of a bone anchor. As used herein, a bone anchor is a device that attaches a suture to the surface of a bone, wherein the suture thus attached does not pass through the bone. The present invention provides devices for connecting sutures to the bone, wherein the sutures have passed through the bone. This is the basis for the distinction, made in this specification, between "bone suture fasteners" and "bone anchors."

A preferred embodiment of the driver 70 of the present invention provides a first jaw 72, whose distal end 74 is adapted for insertion into the vagina 4. (FIG. 8.) An alternative embodiment provides a jaw 72 whose distal end 74 is adapted for insertion into a cavity created in the vaginal hiatus 2 as discussed above. A further embodiment may provide a first jaw 72 whose distal end 74 is adapted for insertion into a transvaginally created cavity in the hiatal plane.

As alternative embodiments to the preferred ratcheting motion of the second jaw 82 toward the first jaw 72, the jaws also may be brought together by various other mechanical advancing means, such as a threaded bar, in combination with a thumb screw. The bone-piercing guide 84 may be hollow or solid; examples of bone-piercing guides 84 may be a needle, a cannula, or a solid rod. The guide 84 also may be a cannula with a removable obturator, so that the guide 84 behaves essentially as a solid rod while piercing the bone, but then can be converted to a hollow configuration for passing various devices along the lumen thereof. A preferred cannula size is believed to be approximately 14 gage. In a preferred embodiment the guide 84 is sharpened and relatively stiff, thus minimizing the possibility that the guide 84 will bend or skim along the surface of the bone, and increasing the tendency of the guide 84 to pierce directly into the bone along a straight line between the first jaw 72 and the second jaw 82.

An advantage of the bone-piercing guide driver 70 is that the device does not require that a hole be drilled through the bone. The passage remains open and completely accessible until the cannula 90 is removed, whereas the drilled hole is often lost once the drill bit is removed. Also, the drill requires additional incisions on both sides of the pubic bone to expose the bone, otherwise tissue is twisted around the drill as it turns.

The driver 70 of this aspect of the invention may be used by itself or in combination with devices of other aspects of the invention. Accordingly, the driver 70 may be used in connection with the dilator 10, for example, by creating a tissue cavity with the dilator 10 and then placing the first jaw 72 of the driver 70 in the tissue cavity created by the dilator 10. Likewise a tissue cavity may be created by the incision guide 50 and the first jaw 72 of the driver 70 may be placed inside the cavity thus created. Furthermore, the insert card 30, capable of introducing into a cavity a medical device, also may be used in connection with the driver 70 of the invention. In this particular combination the first jaw 72 of the driver 70 may be configured to support the card 30 or connect with the articulation opening 40 of the card 30 such that introduction of the first jaw 72 into the tissue cavity places the device in the appropriate position within the cavity. Subsequent operation of the driver 70 directly positions the bone-piercing guide 84 in the proper orientation with respect to the device supported on the card 30. Therefore, use of the driver 70 in combination with devices of other aspects of the present invention may result in several beneficial methods for surgery on the urethral floor and other structures of the pelvis.

This method creates a path through the pubic bone, which path is useful for passing sutures 88 or medical devices through the pubic bone. There are several alternative embodiments of this method. In one embodiment the guide 84 is passed through the bone to create a path through the bone and then the guide 84 is removed, leaving the path in the bone and in the tissue. After removal of the guide 84, medical devices such as a suture 88, a suture passer, or a suture securing device 126 may be passed along the path through the bone that was created by the bone-piercing guide 84. Any device capable of passing a suture through tissue may be used in accordance with the present invention, including the suture passers and methods of their use, disclosed in U.S. Pat. No. 5,611,515, issued Mar. 18, 1997 to Benderev et al., the disclosure of which is incorporated herein by reference.

The driver 70 of the invention also may be used in a different orientation such that the movable jaw is adapted for insertion into a tissue cavity and for driving a device into the pubic bone from the posterior-inferior surface. As an example of a preferred embodiment, a sling 42 with pre-attached push-in bone anchors (not shown) is positioned on an insert card 30 and is placed into a tissue cavity with the assistance of the dilator 10 or the incision guide 50 of the invention, or by using both in combination. Next, the push-in anchors are oriented to face and contact the pubic bone. Finally, the movable jaw of the driver 70 is placed below the push-in anchors of the sling 42 and the fixed jaw of the driver 70 is placed against the patient's abdominal surface such that the pubic bone lies between the fixed jaw and the movable jaw. The movable jaw is then advanced toward the fixed jaw such that the push-in bone anchors are driven into the posterior-inferior surface of the pubic bone and the sling 42 is secured in place.

Other means of securing a sling 42 in place by using push-in type bone anchors are also contemplated in the invention. For example, a pivoting or otherwise manipulable tongue or insert card 30 that supports and positions the sling 42 may be forcefully angled against the pubic bone sufficient to drive into the pubic bone the push-in type anchors from the posterior-inferior surface of the bone. In another embodiment, cannulas 90 are driven through the bone, both left and right of the midline, such that a path into the pubic bone is provided for initial guidance of push-in anchors. As the cannulas 90 on either side of the midline are withdrawn from the pubic bone, the push-in anchors (not shown) are pressed upward against the bone and initially follow the path of the cannulas 90. Thus, a guide hole is created by the cannulas 90 for the anchors. The application of additional upward pressure seats the anchors and the sling 42 is secured in place.

A preferred embodiment of the invention uses a cannula 90 as the bone-piercing guide 84. (FIG. 9*a*.) The lumen of the cannula 90 constitutes a path through the tissue and through the pubic bone. Accordingly, the path through the lumen of the cannula 90 allows passage of sutures 88 or other devices through the bone without the difficulty of locating the path through the bone. (FIG. 9*b*.) In this method a cannula 90 (FIG. 9*a*) is attached to the driver 70, as shown in FIG. 8, and the first jaw 72 of the driver 70 is placed inside the tissue cavity, the pubic bone is located and the driver 70 is positioned to align the pubic bone between the first jaw 72 and the second jaw 82. The second jaw 82 is then advanced toward the first jaw 72, pushing the cannula 90 through the pubic bone and through the soft tissue on either side of the pubic bone. Subsequently, a suture 88 is passed through the cannula 90 and into the cavity.

Depending on the internal diameter of the cannula 90, other devices also may be passed inside the lumen. For example, devices such as a suture passer, a quick connect device, and the like, may be passed through a cannula 90 of sufficient internal diameter. In a preferred embodiment, the cannula 90 has a sharpened tip 96, and has a relatively high degree of stiffness.

This aspect of the invention provides a method of pelvic surgery that uses the driver 70 of the invention wherein the guide 84 of the driver 70 is a cannula 90. The first jaw 72 of the driver 70 is inserted into the tissue cavity, and the pubic bone is located. The driver 70 is positioned to align the pubic bone between the first jaw 72 of the driver 70 and the second jaw 82 of the driver 70. The second jaw 82 is advanced toward the first jaw 72, forcing the cannula 90 into the tissue and through the pubic bone. After the cannula 90 passes through the pubic bone it is further advanced along the same line into the cavity, approaching the first jaw 72 of the driver 70. Alternatively, a first cannula 90 can be used to pierce the pubic bone, and a second cannula 90 may be passed within the lumen of the first cannula 90 to its final position on either side of the urethra. A suture 88 is then passed into the lumen of the cannula 90 and is advanced through the cannula 90 until it enters the tissue cavity. The end of the suture 88 that is in the tissue cavity is secured there and the second end of the suture 88 is secured to the pubic bone. The attachment thus created between the pubic bone and the tissue cavity stabilizes the tissue cavity and structures nearby. (FIG. 10*b*.)

There exist several alternative embodiments of the method of this aspect of the invention. In one embodiment, the cannula 90 is removed after the first end of the suture 88 passes through the cannula 90 and into the cavity. The cannula 90 is therefore withdrawn, leaving both ends of the suture 88 on opposite sides of the pubic bone prior to the attachment of either end of the suture 88 in its place. In another embodiment of this method, the suture 88 is attached within the cavity and then the cannula 90 is withdrawn, followed by the attachment of the second end of the suture 88 to the bone.

The mode of and purpose for attachment of the suture 88 within the cavity is variable, and the factors affecting the selection of the mode will be appreciated by one of ordinary skill in the art. For example, the suture 88 may be affixed in the cavity with one or more stitches 92 (FIG. 10*a*) to tissue therein. Alternatively, the suture 88 may be attached to a device for distribution of pressure across relatively widened area of tissue, such as suture button 94 or a sling 42. (FIG. 9*b*.) The suture 88 also may be attached to a staple (not shown) within the cavity, such that the staple anchors the suture 88, so that appropriate tension on the suture 88 elevates the tissue to which the staple is attached.

Without the use of an additional device, attaching the suture 88 to tissue within the cavity may make possible amelioration of certain incontinence conditions that arise from hypermobility of the urethra or from intrinsic sphincter deficiency. This is done simply by attaching the suture 88 to tissue and then providing an appropriate tension. This tends to elevate the tissue, which therefore elevates the urethra at that position a distance A (compare FIG. 10*a* to 10*b*), eliminating or easing the condition causing urinary incontinence.

An alternative embodiment of this aspect of the invention uses the driver 70 to insert a cannula 90 into the tissue cavity by passing it through the pubic bone as described above. In this embodiment, however, the end of the suture 88 which is advanced through the cannula 90 and into the tissue cavity is passed through a structure 93 within the tissue cavity. It is subsequently passed back out of the cavity and secured to the pubic bone, along with the second end of the suture 88. In this embodiment of the invention, the structure 93 through which the suture 88 may be passed include a suture button 94 or grid, a sling 42, and a tissue mass adjacent the cavity (creating stitches 92). The cannula 90 advantageously has a sharpened end 96 and a reinforced stiffness, to facilitate its passage in a straight line through the bone and to minimize skimming along the surface of the bone. Further, for embodiments of this method, the cavity is preferably a cavity in the vaginal hiatus 2 created according to one of the other methods of this invention. The cavity also may be the vagina 4, or a cavity in the hiatal tissue created transvaginally.

This method is advantageous particularly for the stitching of a tissue mass for stabilization of the urethra floor or other pelvic structures. (FIG. 10*b*.) Because the suture 88 enters and then again exits the tissue cavity, it may be passed through several stitching 92 points in the tissue before it is withdrawn through the cannula 90 and out to the pubic bone. Both ends of the suture 88 may be secured to the pubic bone in a variety of ways, many of which will be explained in detail below.

This method may be advantageously practiced with the additional assistance of a suture passer device. The suture passer is advanced through the cannula 90 and into the tissue cavity upon completion of the desired number of sutured stitches 92 within the cavity, the suture 88 is grasped by the suture passer, and withdrawn through the cannula 90 to properly position it at the surface of the pubic bone for attachment. This method may be preferably used for tensioning, stabilization, or elevation of a tissue mass adjacent to the urethra or adjacent to another soft tissue structure in the pelvis that may be in need of stabilization or reorientation. The fact that the suture 88 is secured to the bone creates a stability for the target tissue mass that is desirable in many cases. It also may be desirable to use this method in securing in a tissue cavity a pharmacological implant, a prosthetic device, or a therapeutic device.

This aspect of the invention provides an additional method for pelvic surgery wherein the driver 70 is used to pass a guide 84 through the pubic bone along a first path, proceeding into the tissue cavity at a first position. A suture 88 is then passed through the cannula 90 into the cavity. The driver 70 is then used to create a second path through the pubic bone, arriving at a second location within the tissue cavity. The suture 88 which was passed along the first path through the pubic bone and into the cavity may then be passed along the second path out of the cavity and through the pubic bone at the second position. Both ends of the suture 88 may then be secured to the pubic bone. In this method, the suture 88 that passes through the cavity may preferably also be passed through a tissue mass of the cavity, a suture button 94 or a grid, or a sling 42, prior to exiting the cavity along the second path through the pubic bone. Alternatively, by simply passing the suture 88 through the cavity and then tensioning it properly, the suture 88 may serve to elevate the tissue mass and stabilize the structures adjacent thereto.

The invention thus provides several alternatives for stabilizing structures of the urethral floor or other structures of the pelvis by securing the soft tissues to the pubic bone. The methods differ primarily in the paths along which the suture 88 is advanced. However, whether one chooses to advance the suture 88 into the cavity and anchor one end of the suture 88 therein, or to advance the suture 88 into the cavity and return it out of the cavity along one path, or to advance the suture 88 into a cavity along a first path and retract it from the cavity along a second path, all three methods may be adapted to several variations. In all of these methods, the tissue cavity may be the vagina 4. It also may be a cavity in the hiatal tissue created, for example, either by the dilator 10 or by the incision guide 50 of the present invention as previously described. Alternatively, the cavity may be a cavity created transvaginally by opening a pocket in the hiatal tissue through the upper vaginal wall 8.

Furthermore, in any of the methods of this aspect of the invention, a preferred embodiment would perform the method on both the right and left side of the midline of the patient, to equally distribute points of attachment on either side of the urethra. Likewise, another preferred embodiment of any of these three methods would involve the additional step of tensioning the suture 88 prior to its attachment to the pubic bone. Suture tensioning may be accomplished in a variety of ways, one of which is with the use of suture tensioning device. This type of device has a handle with which the surgeon can place the device next to the location where the suture 88 will be tied. Attached to the handle is another structure of the suture tensioner around which the suture 88 will be wrapped, and upon which the suture 88 may be tied. The external dimensions of this structure control the degree of slack that the suture 88 retains after the suture 88 is tied. Therefore, based on the linear distance between the bone and the soft tissue sought to be stabilized, as well as the amount of slack needed to achieve a particular objective for a given patient, a suture tensioner with an appropriate diameter will be selected so as to provide the proper amount of tension in the connection between the bone and the soft tissue.

The several methods of passing a suture 88 through one or more paths in the pubic bone may be particularly applied to a method for stabilizing a urethral sling 42 relative to the pubic bone. In this method a cavity is created in the vaginal hiatus 2. The cavity may preferably be made using the dilator 10 or the incision guide 50 of the present invention, or both in combination. The dimensions of the cavity and the amount of offset from the urethra will be determined according to the size of the sling 42 that is needed, the dimensions of the patient's urethra, and the surgeon's preference. After the cavity is formed, guide 84 is driven through the pubic bone to create a path. This is done by placing the distal end 74 of the first jaw 72 of the driver 70 into the tissue cavity followed by positioning the second jaw 82 of the driver 70, such that the pubic bone lies in a straight line between the first jaw 72 and second jaw 82. A urethral sling 42 is placed into the cavity either before or after the cannula 90 is driven through the pubic bone and into the cavity. The sling 42 may be placed into the cavity with the aid of an insert card 30 as discussed above, or by other surgical procedures known in the art. With the cannula 90 in the cavity adjacent the sling 42, the suture 88 is attached to the sling 42 and to the pubic bone.

This method is embodied in a technique wherein the cannula 90 is withdrawn before the suture 88 is secured on either end. The method also contemplates withdrawal of the cannula 90 after the sling 42 is secured but before the suture 88 is secured to the bone. In addition to attaching the sling 42 with sutures 88, this method contemplates an indirect attachment of the sling 42 to sutures 88 by directly attaching the sling 42 to devices which are themselves attached to sutures 88. An example of such an indirect attachment to a suture 88 is a securing device 126 as disclosed herein. This method may advantageously involve use of the devices of other aspects of the present invention. The tissue cavity may be made either by the dilator 10 or the incision guide 50, or by using both together, and the sling 42 may be delivered to its proper position in the cavity with aid of the insert card 30 as discussed above. Depending on the particular manner in which the insert card 30 articulates with a driver 70, the cooperative use of the insert card 30 may precisely position the sling 42. This will cause the bone-piercing guide 84 to meet the sling 42 at the appropriate straight line position as is desirable in this method.

Another aspect of this invention provides a driver frame assembly 100. The driver frame assembly 100 FIG. 13, serves to align, support and stabilize both the patient's pelvis and the devices of the invention in procedures for reconstructing the urethral and pelvic floor or for performing other methods of pelvic surgery. The driver frame assembly 100 has an upper clamp 102, a rigid catheter 52, a cavity tongue 114, a lower clamp 120, and at least one driver 70. The upper clamp 102 of the driver frame assembly 100 has a head portion 104, a descending arm 106 and a base portion 108. The head portion 104 has a compression foot 110 that is used to compress a patient's abdominal surface against the pubic bone. The compression foot 110 has stabilizing pins 112 that extend downward therefrom and that pierce the patient's skin 48, penetrating the abdomen at a position adjacent to the superior surface of the pubic bone. The compression foot 110 may be pressed against the abdomen of the patient with, for example, a threaded screwing mechanism, a ratcheting or piston mechanism, or a linkage mechanism. The stabilizing pins 112 are designed to be of a length that makes it impossible for the pins 112 to cause damage to any abdominal or pelvic organs. At the same time the stabilizing pins 112 have dimensions making them sufficiently strong to resist the lateral forces exerted with operation of the driver 70.

Figure 11:
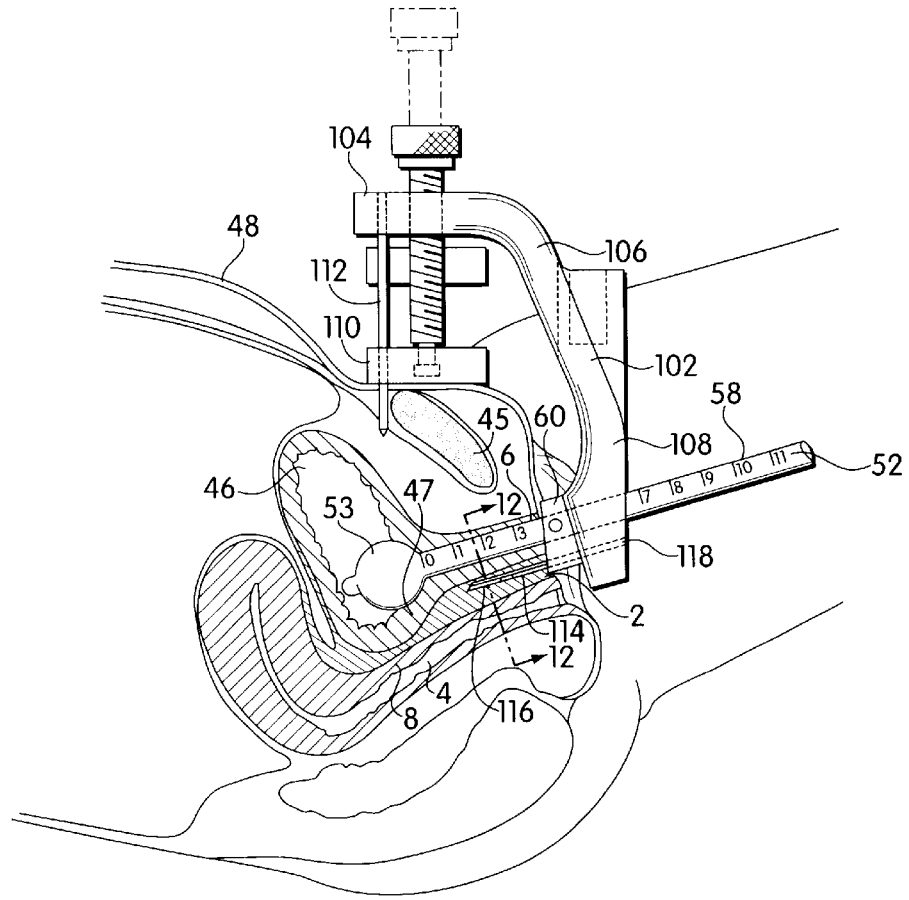
FIG. 11 is a cross section view of the pelvis as in FIG. 3 with the upper clamp of the driver frame assembly in place, articulating with the rigid catheter and the tongue.

The rigid catheter 52 portion of the driver frame assembly 100 functions much as the rigid catheter 52 of the incision guide 50, as discussed above. The catheter 52 is intended to straighten and elongate the urethra, as well as to assist in identifying the position of the urethra, the bladder 46, and bladder neck 47. The rigid catheter 52 is of sufficient length to extend outward beyond the distal urethra of the patient. This external extension of the rigid catheter 52 provides a structure with which the frame assembly may articulate and attach. (FIG. 11.)

Figure 12A:
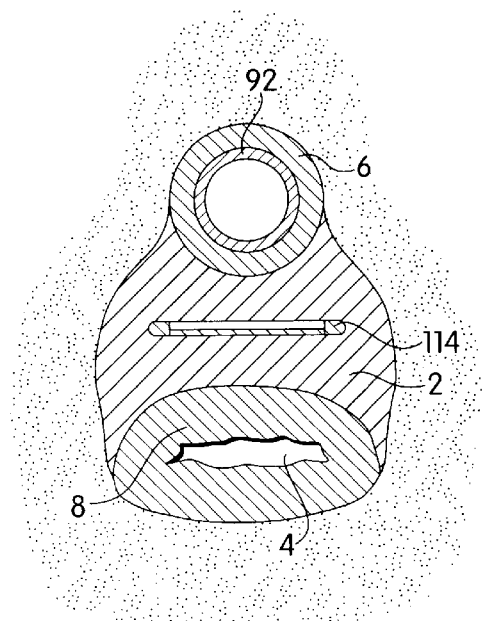
FIG. 12a is a cross section taken along the line 12—12 in FIG. 11, and illustrates the hiatal region depicting a flat insertion tongue.
Figure 12B:
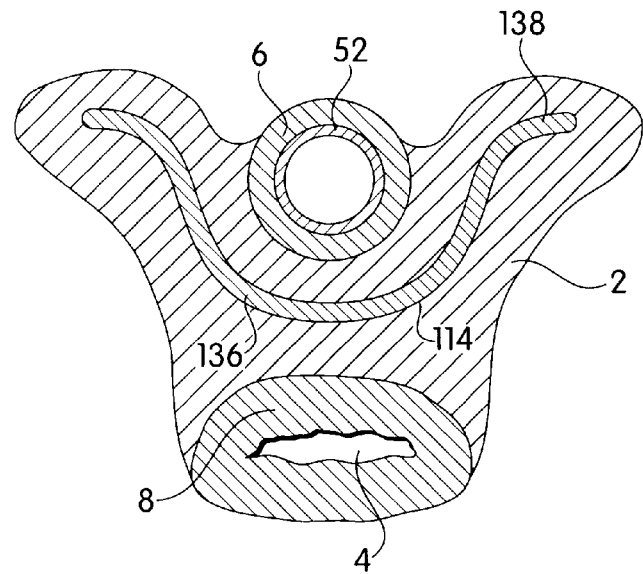
FIG. 12b is a cross section taken along the line 12—12 in FIG. 11, and depicts a concave insertion tongue in a hiatal cavity.
Figure 15:
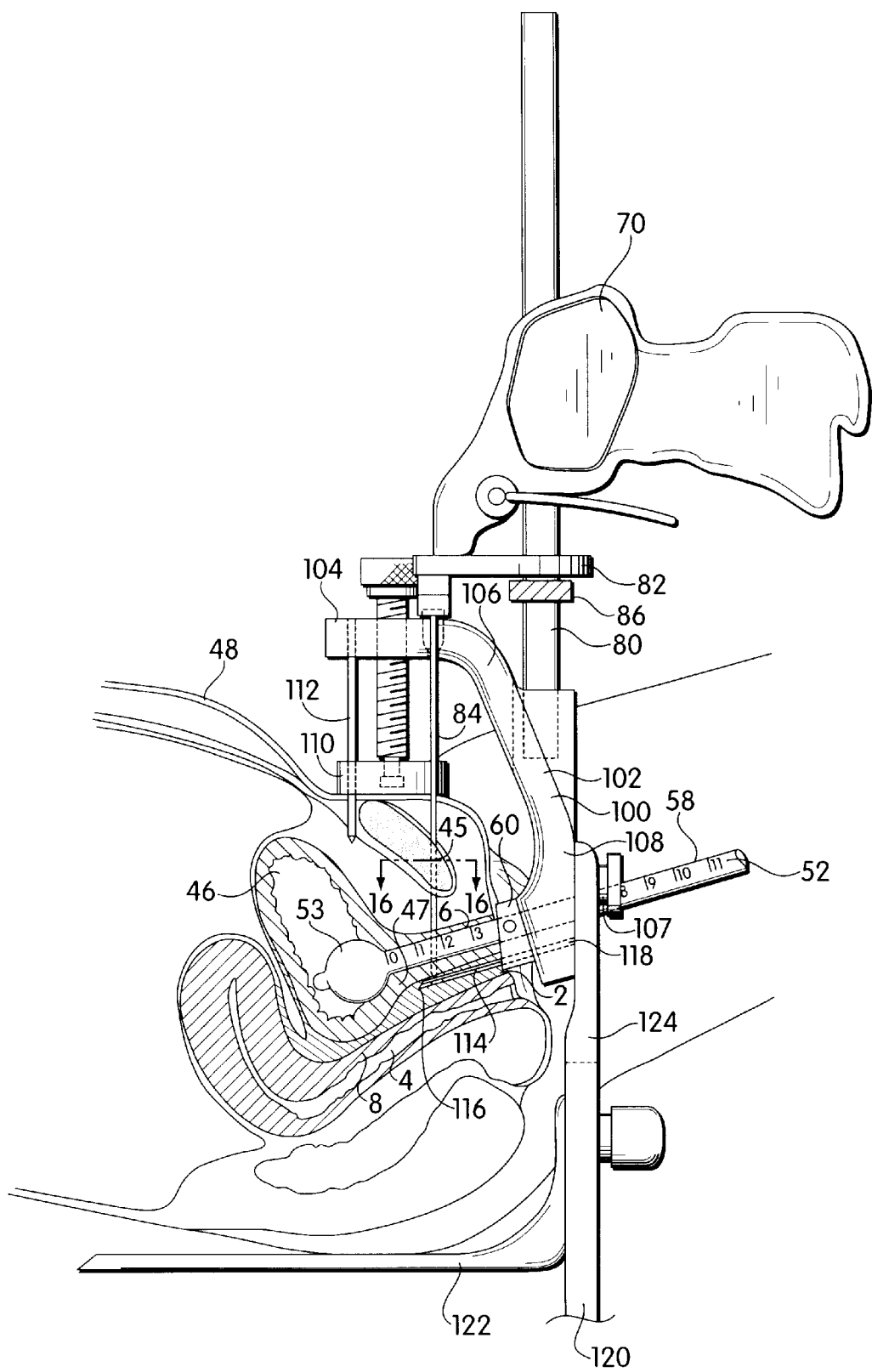
FIG. 15 is a cross section as in FIG. 3, and depicts the driver frame assembly with the bone-piercing guides penetrating to the hiatal cavity.

The tongue 114 portion of the driver frame assembly 100 is adapted for insertion into a tissue cavity, such as the vagina 4 or a hiatal cavity prepared prior to insertion of the tongue 114. In a preferred embodiment, the tongue 114 has a central depression 136 and elevated edges 138 (FIG. 12*b*), allowing compression of the tongue 114 sides against the inferior surface of the pubic bone to counter the pressure of the compression foot 110. Because of the shape of the tongue 114, this type of pressure may be applied without crushing the urethra. The tongue may also have a relatively broad elevated edge 138 contact pins 140 for contacting the pubic bone. (FIGS. 24 and 25.) A flat tongue 114 does not allow the application of a strong counterpressure against the bone, because of the potential damage to the urethra. (FIG. 12*a*.) The tongue 114 has a first end 116 for inserting into the cavity, and a second end 118 which is adapted for articulating with the base portion 108 of the upper clamp 102. This articulation may be, for example, by means of a threaded connector 107 that joins the tongue 114 to the base portion 108 of the upper clamp 102 (FIG. 15.).

Figure 13:
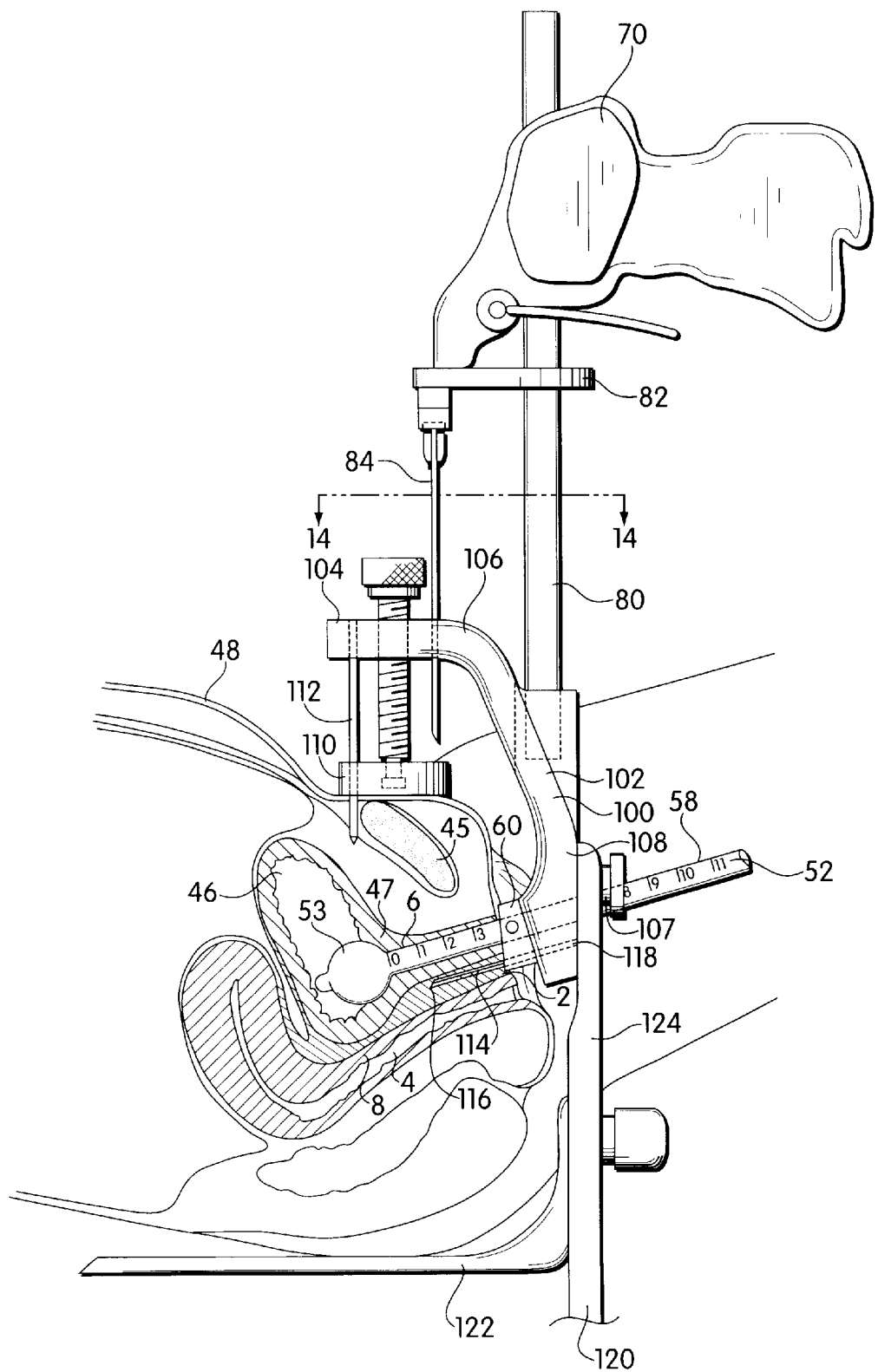
FIG. 13 is a cross section view of the pelvis as in FIG. 3 showing the complete driver frame assembly in place.

The lower clamp 120 of the driver frame assembly 100 has a buttock plate 122 for insertion beneath the patient such that the patient's weight rests on the plate to further secure the frame assembly. Attached to the buttock plate 122 is an ascending arm 124 that is adapted for articulating with the base portion 108 of the upper clamp 102. (FIG. 13.) Thus, the upper clamp 102 attaches to the rigid catheter 52 and the cavity tongue 114, and then the upper clamp 102 also attaches to the lower clamp 120, which is anchored under the patient's body. The effect of these multiple attachments is to compress a patient's pelvic region to provide stability for operation of the bone-piercing guide driver 70 as well as to enhance the straight line precision of driving a guide 84 through the pubic bone.

Figure 18:
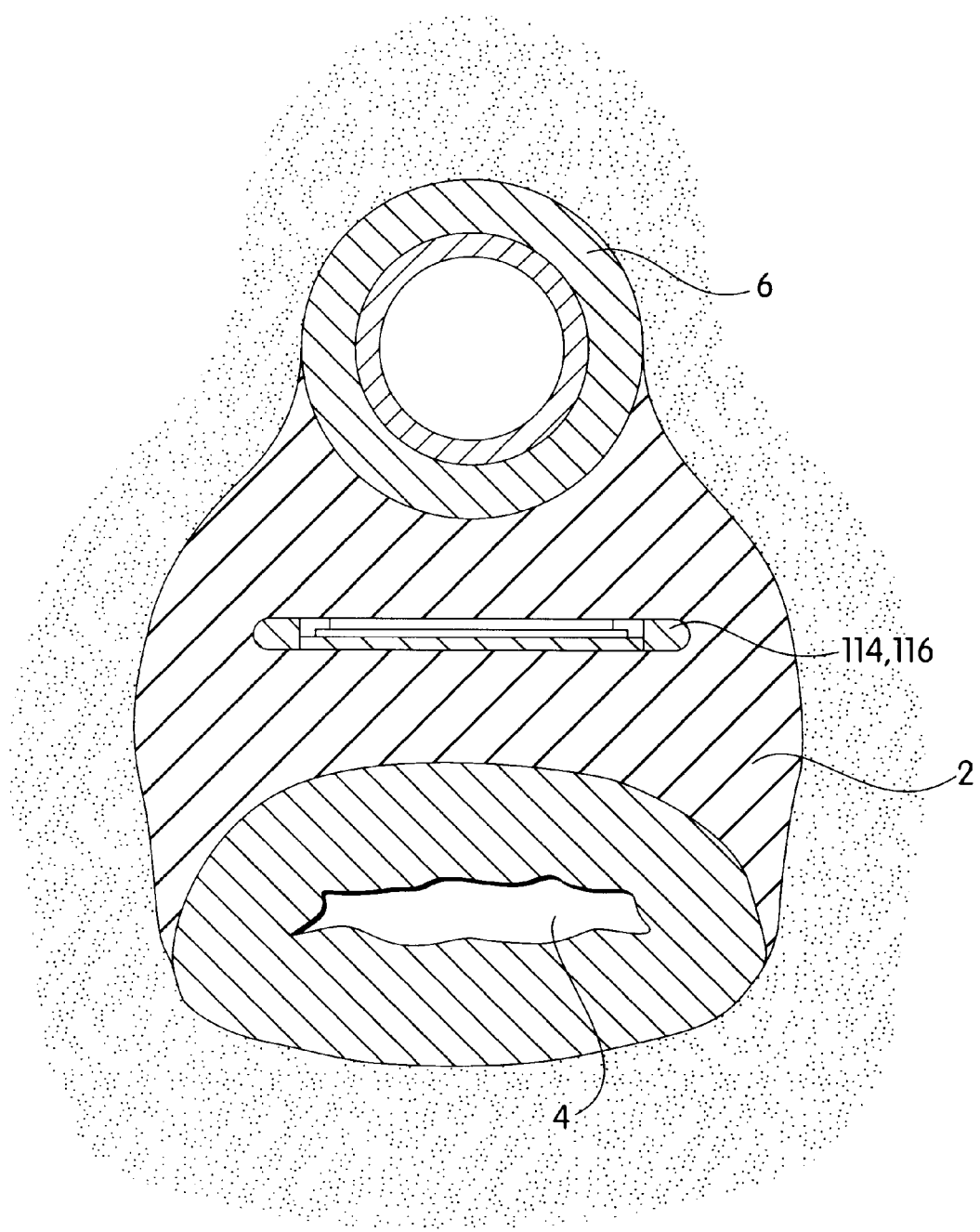
FIG. 18 is a cross section taken along the line 19—19 in FIG. 17, and shows the position of the rigid catheter inside the urethra, the tongue, the insert card, and the sling.

In a preferred embodiment, an insert card 30 capable of supporting a medical device is an additional component of the driver frame assembly 100. (FIG. 18.) In such an embodiment, the card 30 adapted to slide along the tongue 114 to reach the proper position within the cavity. The articulation opening 40 of the card 30 also may be used for attachment or positional control of the card 30 with respect to the driver frame assembly 100.

The driver 70 portion of the driver frame assembly 100 is similar to the driver 70 of a previous aspect of the invention as discussed above. The driver 70 of this aspect of the invention, however, does differ in the respect that it attaches to the driver frame assembly 100 via the slide bar 80 of the driver 70. Accordingly, the driver 70 of this aspect of the invention has the slide bar 80 and the moveable jaw, but does not have its own immovable or first jaw 72. However, upon attachment of the driver 70 to the driver frame assembly 100, both the tongue 114 portion and the buttock plate 122 portion of the driver frame assembly 100 can simultaneously function as fixed jaws toward which the immovable jaw advances as it moves along the slide bar 80. (FIG. 15.)

Figure 14:
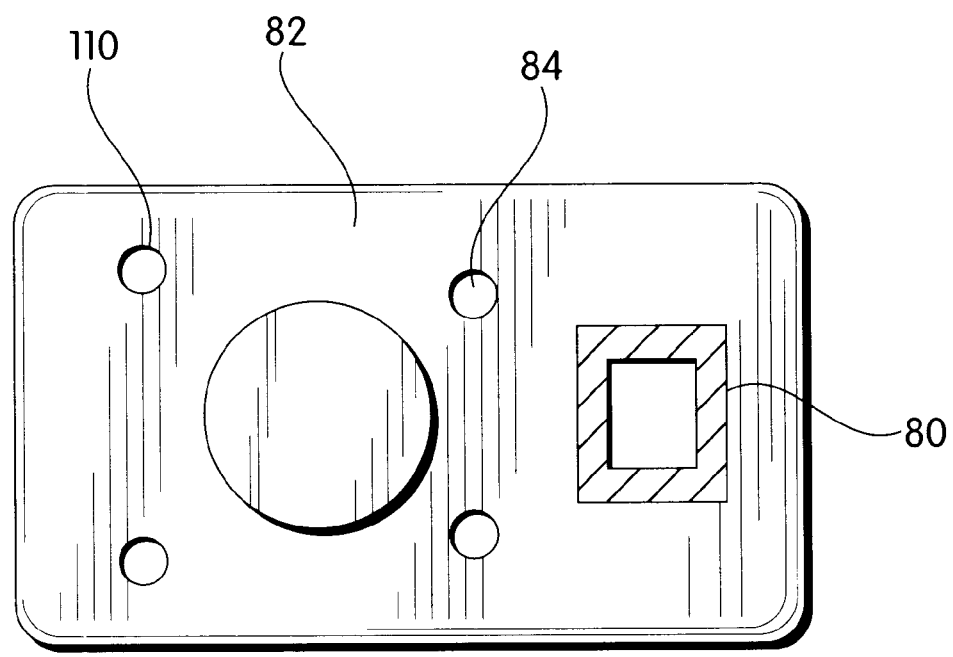
FIG. 14 is a cross section view taken along the line 14—14 in FIG. 13, showing left and right displacement of the bone-piercing guides mounted on the driver.
Figure 16:
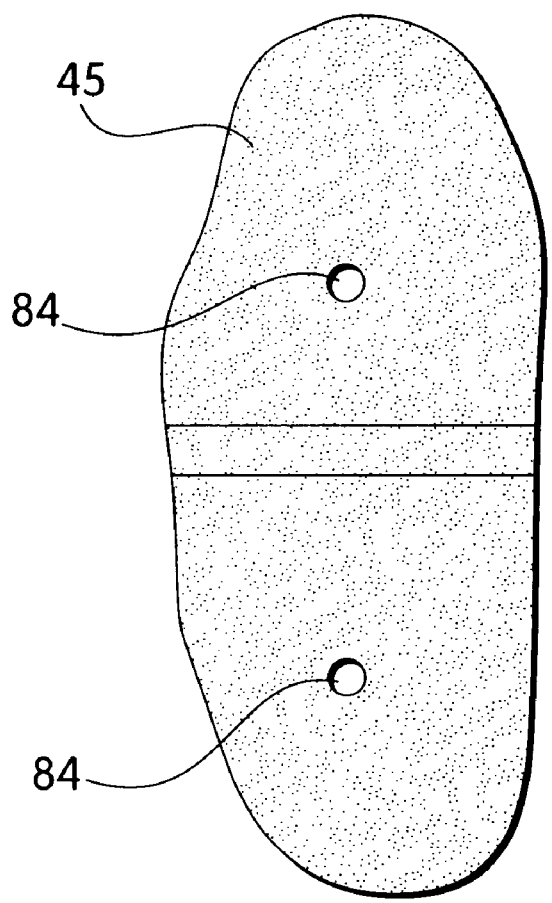
FIG. 16 illustrates the pubic bone with the guides passing through the bone left and right of the pubic symphysis.

As mentioned above, the function of the first or fixed jaw is to provide counterpressure to the pressure applied to the pubic bone by the advancement of the guide 84 through the pubic bone. The preferred driver 70 portion of the driver frame assembly 100 has two positions for attachment of bone-piercing guides 84 to the second, or movable, jaw 72. (FIG. 14.) These positions are left and right of center, being laterally spaced to provide sufficient offset from the patient's midline so as to prevent any contact of the bone-piercing guides 84 with the urethra. Thus, the driver 70 of the assembly is intended to simultaneously advance two separate bone-piercing guides 84 through the pubic bone, one left and one right of the patient's midline, as shown in FIG. 16.

Figure 12C:
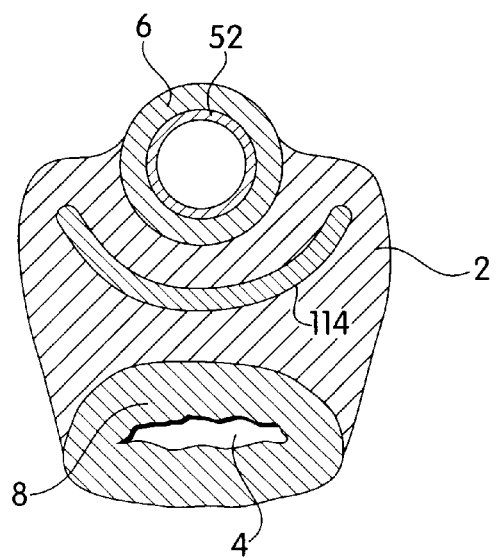
FIG. 12c is a cross section taken along the line 12—12 in FIG. 11, and depicts a concave insertion tongue in a hiatal cavity.

This aspect of the invention provides a method for reconstruction of the urethral and pelvic floor or for stabilizing a tissue of the pelvic region. In this method a rigid catheter 52 is placed in the urethra so that the urethra is elongated and straightened. (FIG. 11.) The catheter 52 also aids in determining the position of the bladder 46 and the bladder neck 47. The tongue 114 of the driver frame assembly 100 is placed into the tissue cavity, and also may be attached to the rigid catheter 52. (See FIGS. 11 and 12.) Preferably an insert card 30 holding a medical device, for example, a urethral sling 42, is inserted into the cavity using the tongue 114 as a guide. (FIG. 18.) The upper clamp 102 is attached to the tongue 114 and to the catheter 52, and the compression foot 110 is compressed against the patient's abdomen, after palpation to determine the proper position of the stabilizing pins 112 relative to the superior surface of the pubic bone. The compression foot 110 is tightened against the patient's abdomen to prevent slipping of the bone-piercing guide 84, and to further immobilize the soft tissues of the pelvis. (FIG. 11). Further stabilization is achieved with attachment of the lower clamp 120 which is done by sliding the buttock plate 122 beneath the patient and firmly attaching the ascending arm 124 of the lower clamp 120 to the base portion 108 of the upper clamp 102. (FIG. 13.)

With the driver frame assembly 100 properly installed along the patient's midline, the driver 70 portion of the driver frame assembly 100 may be mounted on the descending arm 106 of the upper clamp 102. (FIG. 13.) Care is taken to assure that the bone-piercing guides 84 of the driver 70 are positioned such that they will enter the pubic bone. Then the second removable jaw of the driver 70 is advanced downward along the slide bar 80 and the guides 84 are advanced into the abdominal surface and through the pubic bone, emerging within the tissue cavity near the medical device supported on the card 30. (FIG. 15.)

Figure 17:
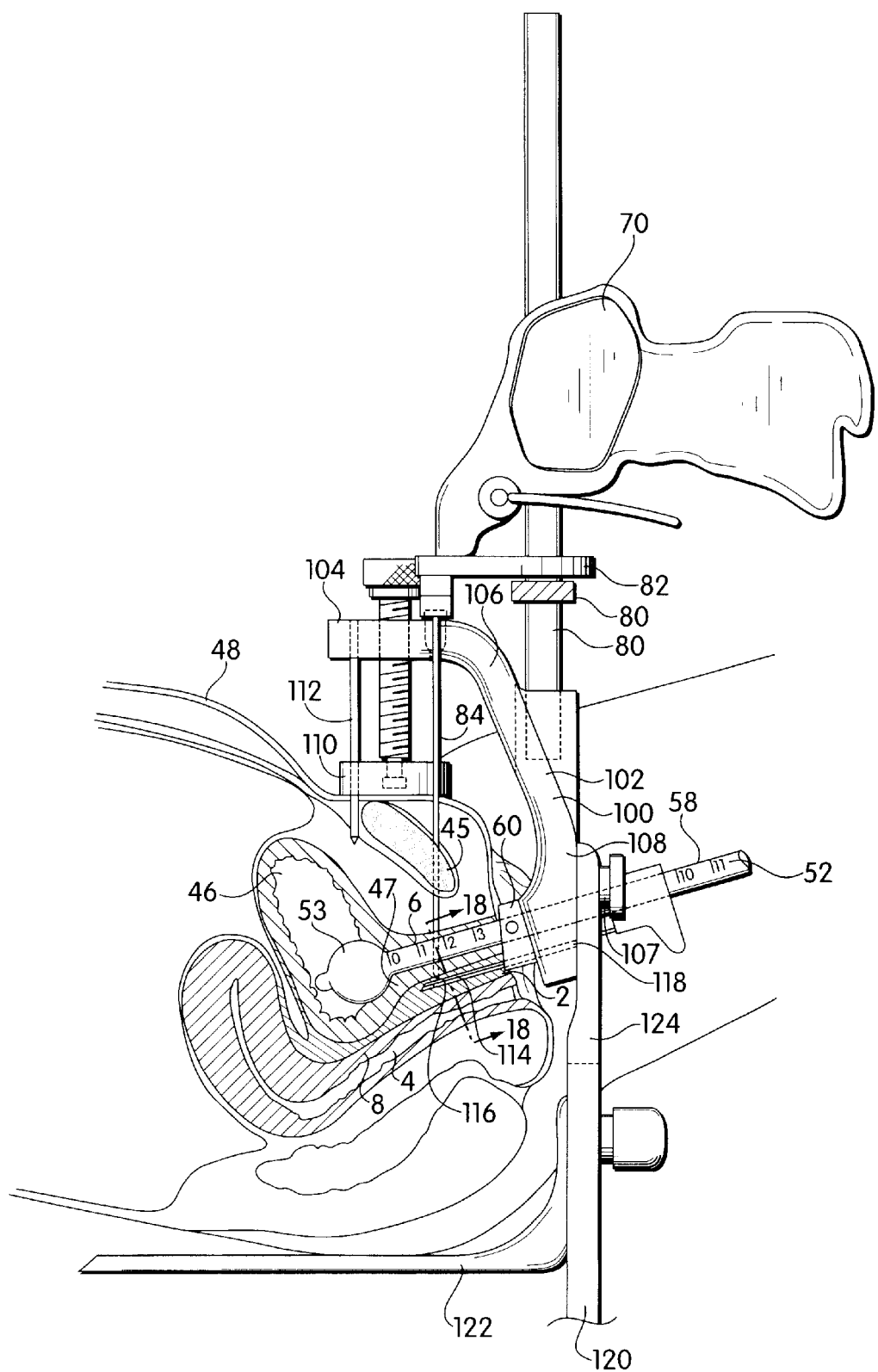
FIG. 17 is a cross section view of the pelvis as in FIG. 3 and the driver frame, with the tongue supporting an insert card and a sling in position.
Figure 19:
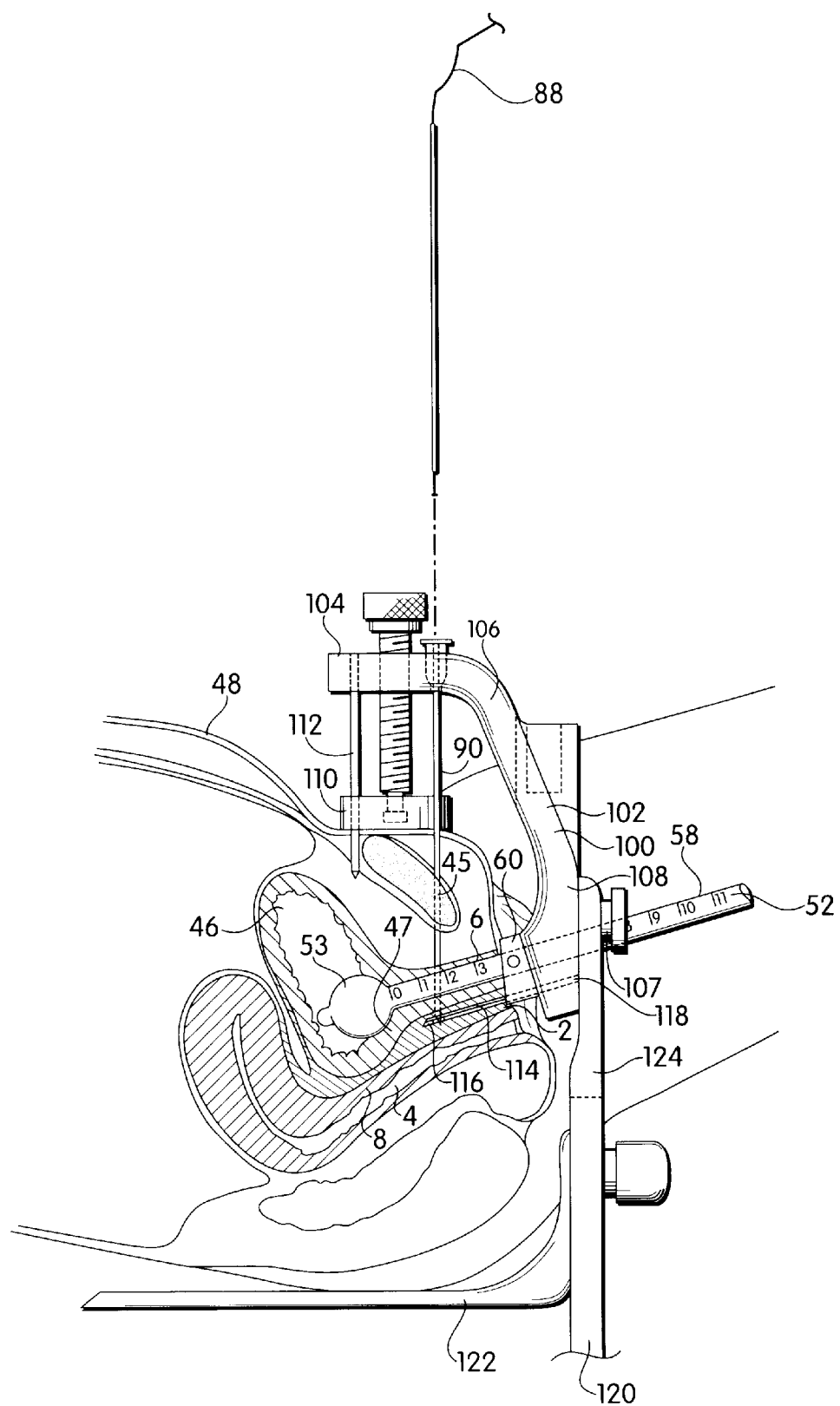
FIG. 19 is a cross section as in FIG. 17 with the driver frame in place, and shows the driver frame with the driver removed and a cannula in position.

In a preferred example, the bone-piercing guides 84 are cannulas 90 and the medical device supported on the card 30 is a sling 42. (FIGS. 17 and 18.) In such an embodiment, the proximity of the cannulas 90 with the sling 42 permits suturing or other attachment through the lumen on the cannula 90 to the desired location on the urethral sling 42. (FIG. 19.) After attachment of suture 88 directly or indirectly (see FIGS. 21–23) to the sling 42, the cannulas 90 are removed, leaving behind the suture 88, which is then secured to the pubic bone. (FIG. 27.)

In another embodiment of this aspect of the invention, a concave insertion tongue 114 is used to provide counterpressure for driving cannulas 90 through the pubic bone 45. The concave tongue 114 is inserted into a cavity, such as, for example, a hiatal cavity or the vagina 4, and the compression foot 110 of the driver frame assembly 100 is placed against the patent's pubic bone 45. (FIG. 24*a*.) The concave tongue has a central depression 136 and elevated edges 138, allowing the edges 138 of the tongue 114 to provide counterpressure to the posterior/inferior surface of the pubic bone 45, while the compression foot 110 and the cannulas 90 apply pressure to the opposite (anterior/superior) surface of the bone 45. (FIG. 24*b*.)

The central depression 136 of the tongue 114 prevents the urethra 6 from being crushed upon application of counter pressure on the bone 45 by elevated edge 138 of the tongue 114. (FIG. 24*b*.) The edge of the tongue may also have a gap 144 to allow the cannula 90 to pass through the plane of the elevated edge 138 without the cannula 90 impacting against the tongue 114. The edge 138 may also have contact pins 140 of a configuration and position to pierce through soft tissue and fascia to contact the surface of the pubic bone 45 and prevent slippage of the tongue 114. (FIG. 25.)

Figure 24B:
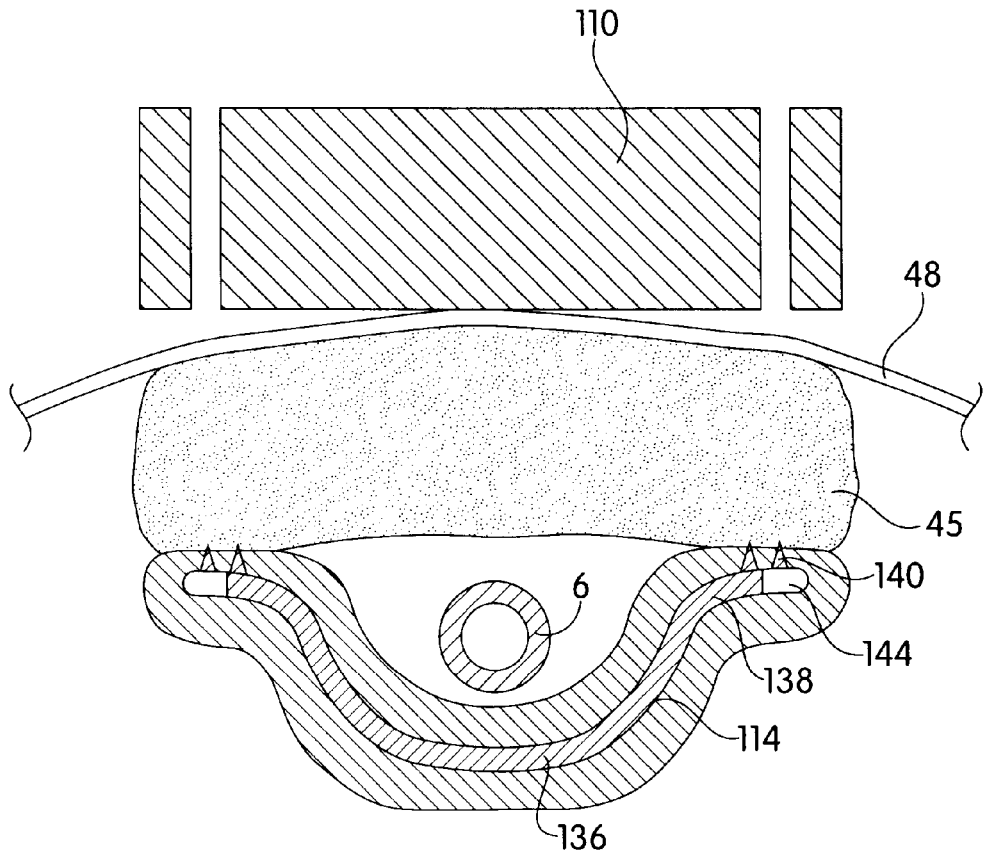
FIG. 24b corresponds to FIG. 24a and shows the concave tongue and contact pins providing counterpressure against the inferior posterior face of the pubic bone.
Figure 26A:
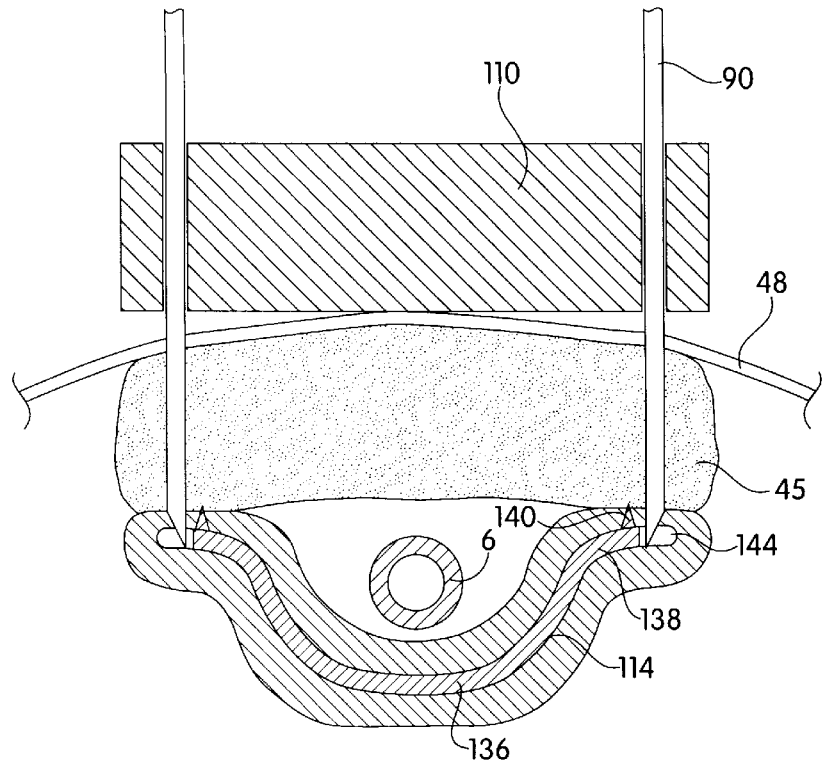
FIG. 26a corresponds to FIG. 24b, and shows the compression foot with bone driver guides passing through the pubic bone and passage gap of the tongue.
Figure 26B:
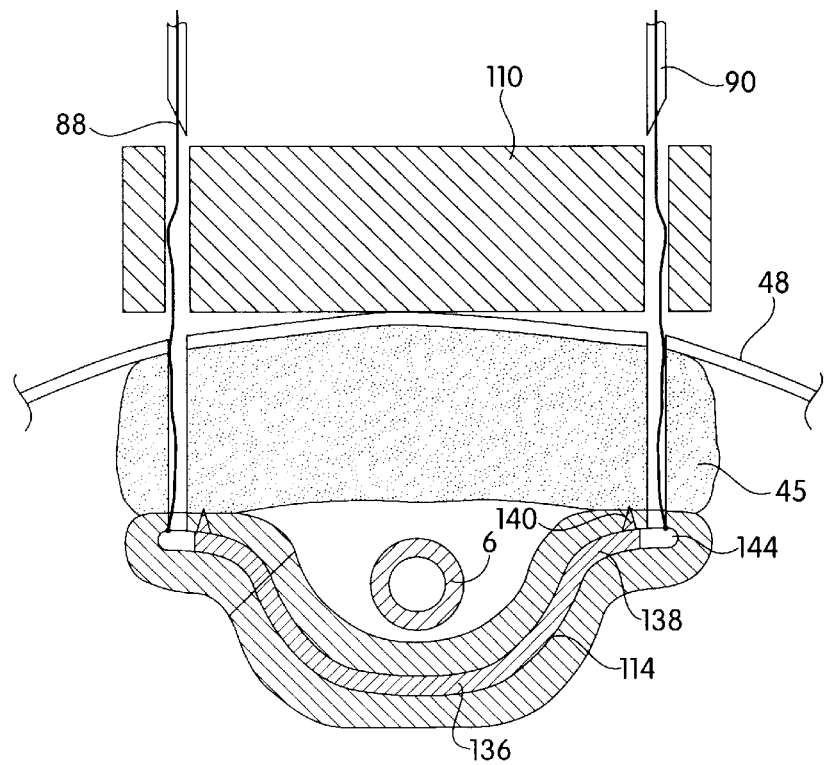
FIG. 26b corresponds to FIG. 26a, and shows the withdrawal of the guides and the position of the sutures.

When pressure is applied to the opposite sides of the bone 45, as shown in FIG. 24*b*, the cannulas 90 are driven through the pubic bone 45 and into the cavity. (FIG. 26*a*.) Suture 88 or other devices may be passed through the cannulas 90 and into the cavity. (FIG. 26*b*.) The suture 88 may be attached within the cavity either by stitches 92 or by attaching the suture 88 to a suture button 94. (FIG. 26*b*.)

Figure 27A:
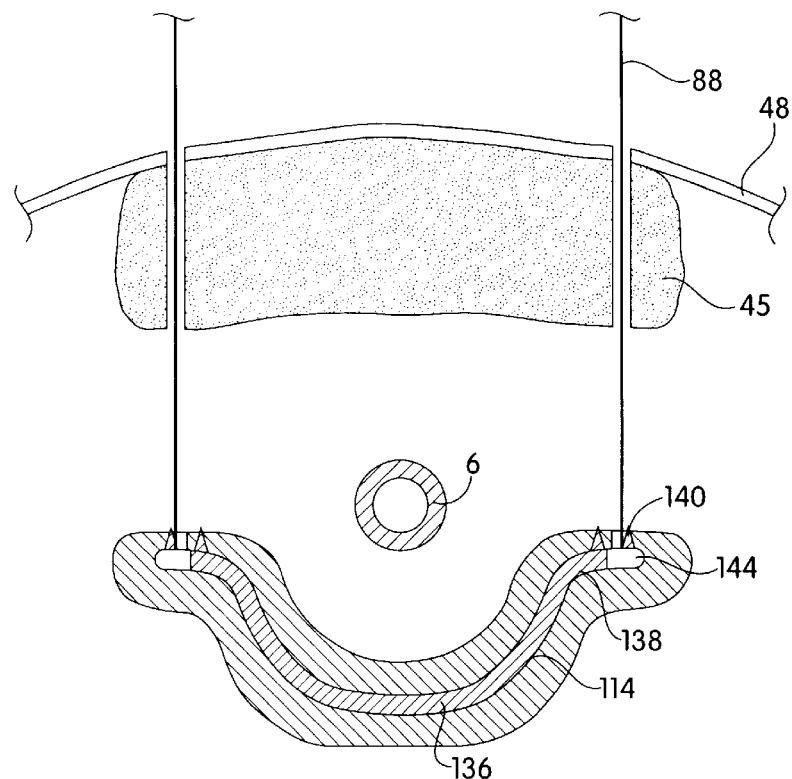
FIG. 27a corresponds to FIG. 26b, and shows the orientation of the sutures, the tongue, and the hiatal cavity before tensioning of the sutures.
Figure 27B:
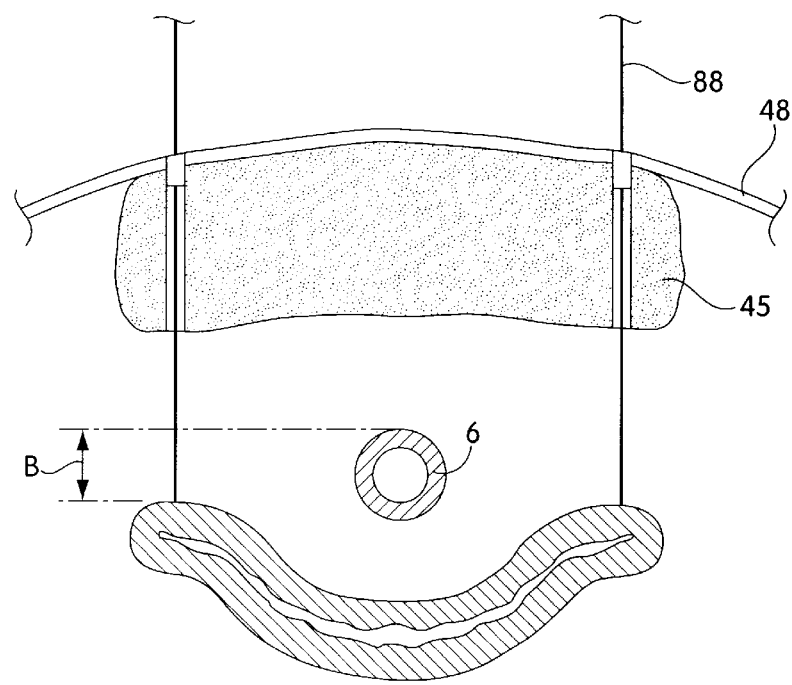
FIG. 27b corresponds to FIG. 27a, and shows the elevation of the hiatal cavity and the urethra after tensioning of the sutures.

After proper attachment of the suture 88 within the cavity, the pressure on both sides of the bone 45 is released, and the compression foot 110 is raised. (FIG. 27*a*.) The tongue 114 is removed from the cavity, and the sutures attached therein are fastened to the bone 45 with, for example, either a bone eyelet 150 or a bone suture fastener 170. The urethra 6 is elevated by the tension that is applied to the sutures 88 in the step of fastening the sutures 88 to the bone 45. The resulting elevation of the urethra 6 is shown as distance B in FIGS. 27*a* and 27*b*.

The advantage of the method of this aspect of the invention is that the driver frame assembly 100, if properly installed, provides rigidity to the driver 70 to allow for highly accurate straight line passage of a bone-piercing guide 84 through the pubic bone and to a target sight within the soft tissue. Because the driver 70 is able to advance two different guides 84 through the bone at the same time, and because the contact between the guide 84 and the sling 42 is relatively precise, the entire procedure can be done very rapidly and with minimal invasion compared with other procedures used to achieve a similar objective. In addition, the method of this aspect of the invention, being minimally invasive, greatly reduces the risk of infection arising from the procedure. Also reduced is the number of incisions, resulting in a shorter recovery time for the patient and less scarring, since the external abdominal wounds are all puncture wounds, and the only incision is a relatively small incision or a knife stick in the vaginal hiatus 2 or in the upper vaginal wall 8. In a preferred embodiment of this aspect of the invention, the sutures 88 which pass through the bone are secured to the bone after being tensioned with a suture tensioning device as discussed above.

Figure 21:
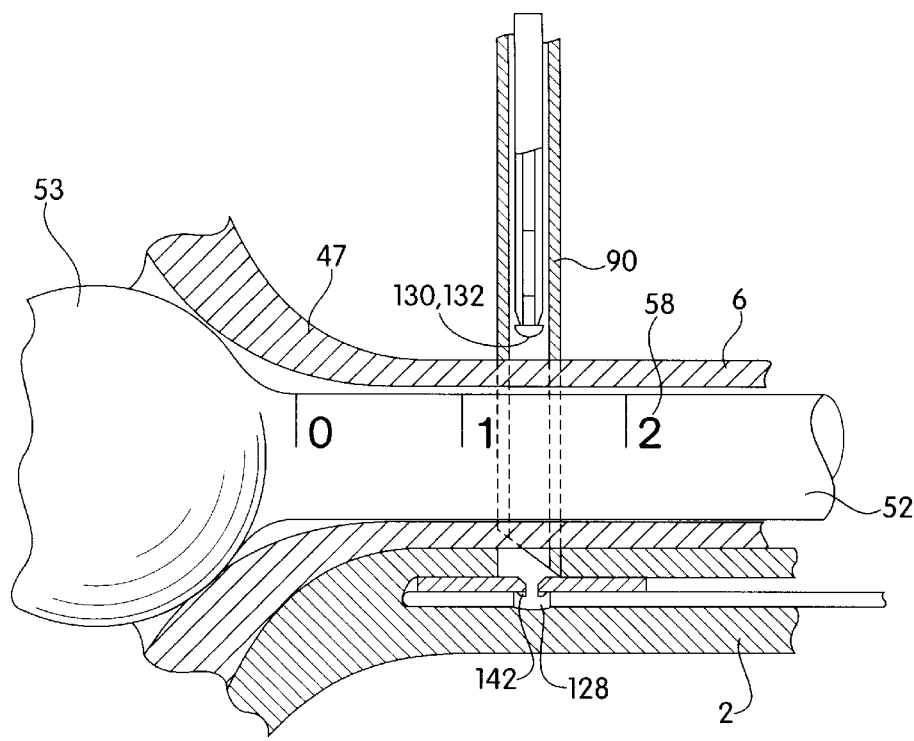
FIG. 21 is a detail view of the area described by the curved arrows in FIG. 20, and shows detail of the quick-connect device passing through the cannula toward the sling.
Figure 22:
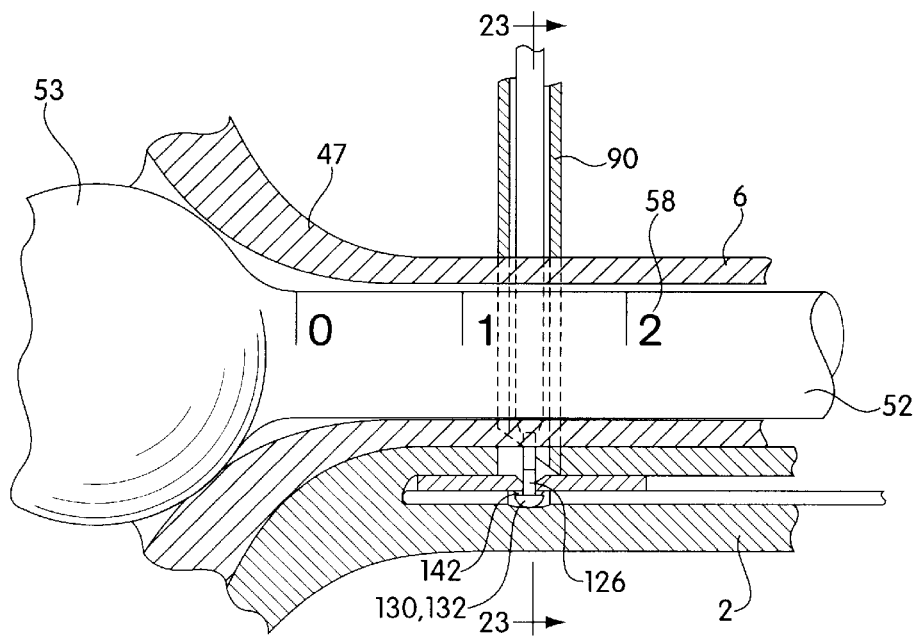
FIG. 22 corresponds to FIG. 21, and provides detail of the quick-connect device articulating with the ring member of the sling.
Figure 23:
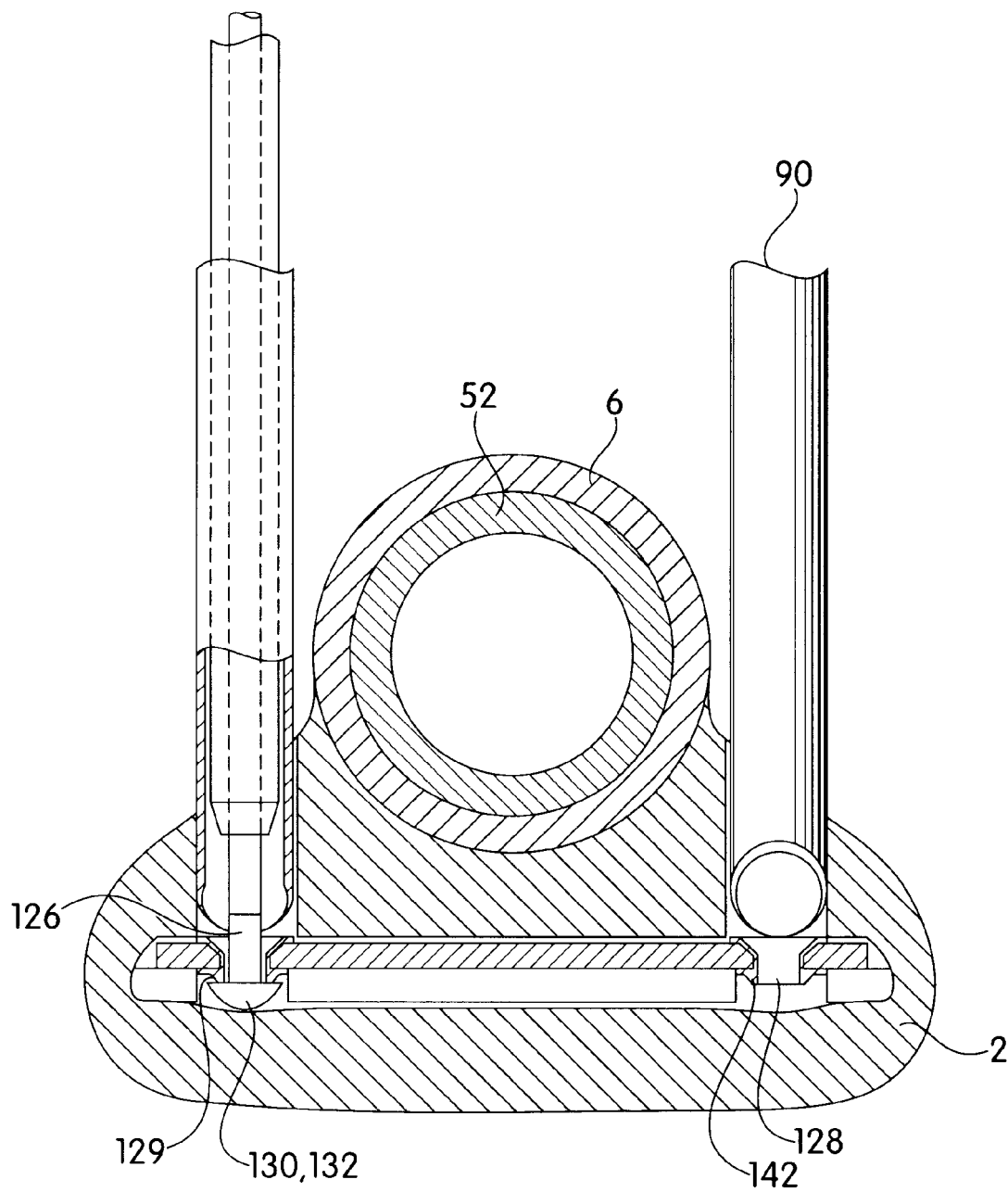
FIG. 23 is a cross section taken along the line 23—23 in FIG. 22, and shows the position of the rigid catheter, left and right side cannulas, and a quick-connect device in the left cannula articulated with the ring member of the sling.

Another aspect of the invention provides a system for attaching urethral sling 42 to a suture 88 as shown in FIGS. 21–23. The system includes a urethral sling 42 and a connector 130; the urethral sling 42 has a ring member 44 attached thereto (FIGS. 29–30) and the connector 130 is adapted to cooperate with the ring member 44 to permit unidirectional passage of the connector 130 through the ring member 44 (FIGS. 21–23, 32–35). The ring member 44 and the connector 130 further cooperate to prevent retrograde movement of the connector 130 through the ring member 44.

Figure 29:
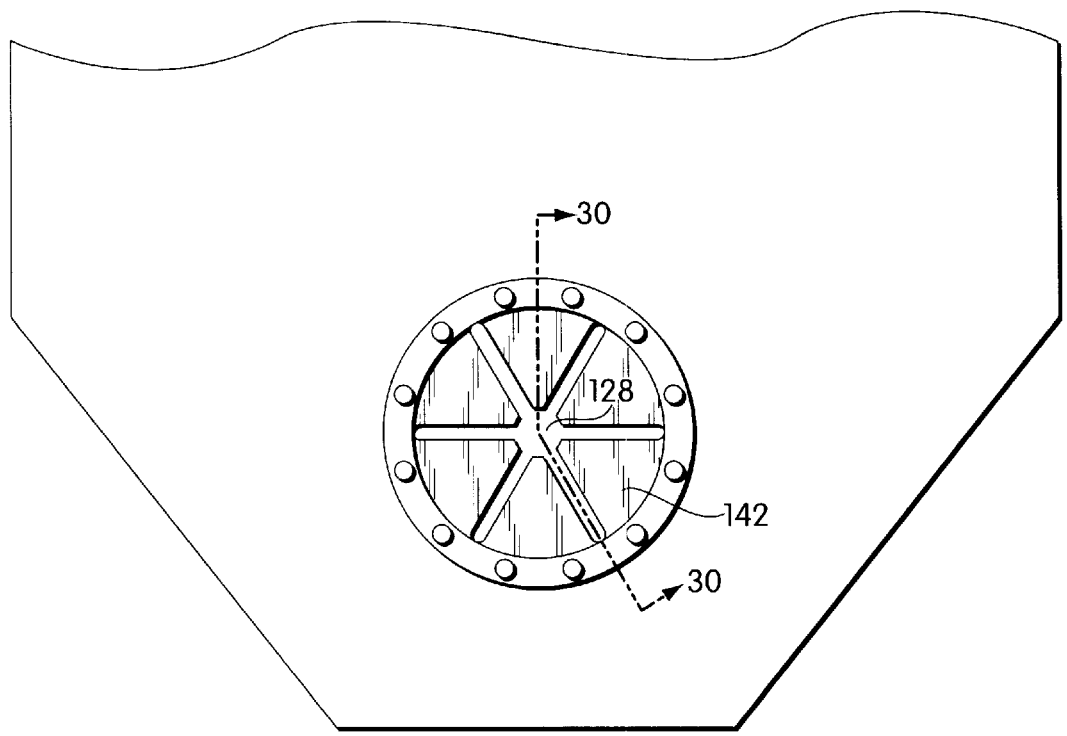
FIG. 29 is a plan view of a sling with the ring member of a quick-connect device in place.
Figure 30:
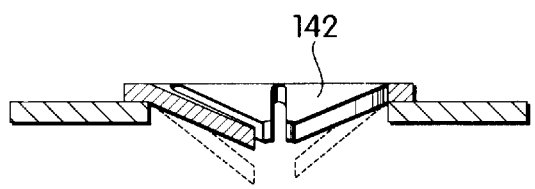
FIG. 30 is a cross section view taken along the line 30—30 in FIG. 29, showing the sling with the quick-connect ring member in place.
Figure 32:
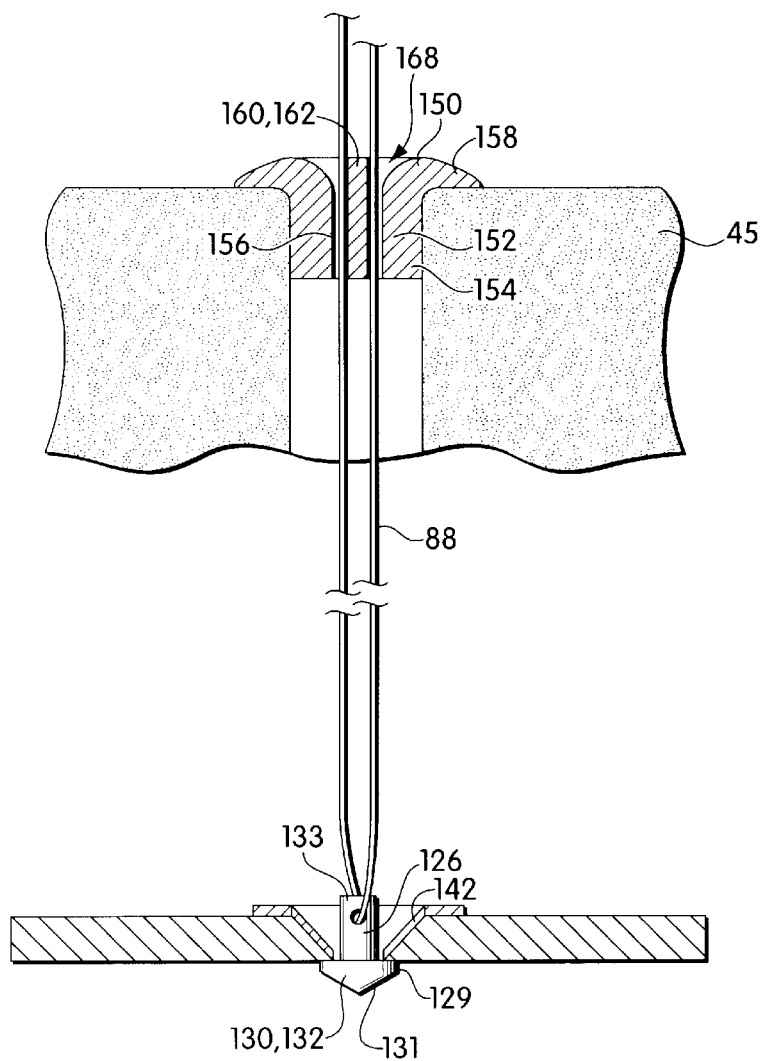
FIG. 32 is a cross section taken along the line 32—32 in FIG. 31, and depicts the bone eyelet with a planar crosspiece in position in the pubic bone and connected by suture to an arrowhead configuration of the quick-connect device articulated with the ring member of the sling.
Figure 33:
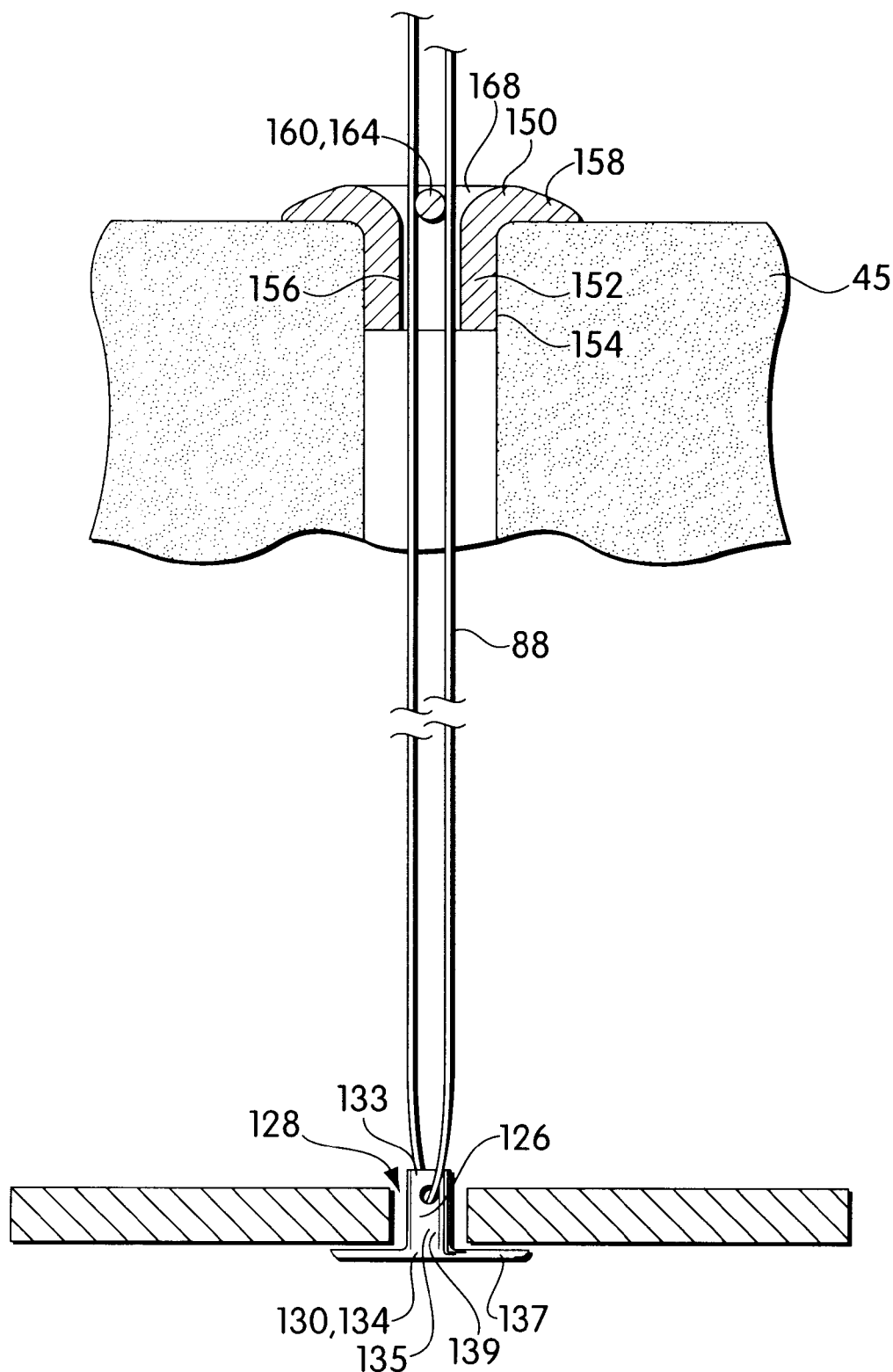
FIG. 33 corresponds to FIG. 32a, but shows a bone eyelet with a rod crosspiece in place in the pubic bone connected via suture to a T-configuration of the quick-connect device.
Figure 34:
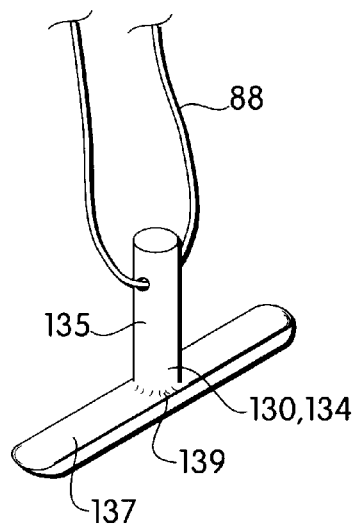
FIG. 34 is a perspective view of the T-configuration of the quick-connect device.
Figure 35:
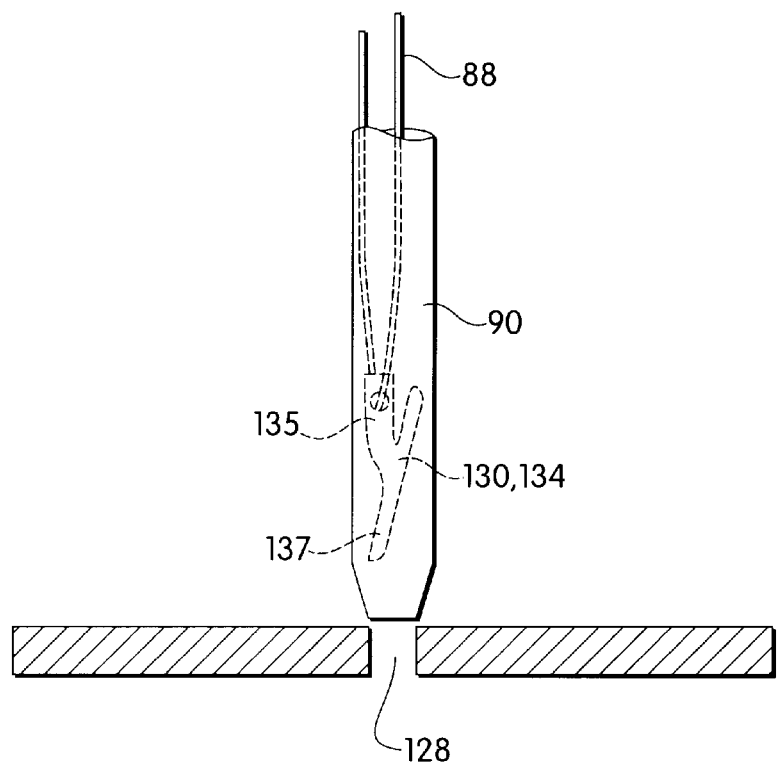
FIG. 35 is a side elevation that depicts the passage of the T-configuration of the quick-connect device through a cannula toward the ring member of a sling.

The invention contemplates several embodiments both of the ring member 44 and of the connector 130. The ring member 44 may be as simple as a hole in an appropriate part of the sling 42, suited for passage therethrough by a connector 130. (FIGS. 33–35.) The ring member 44 also may be a more elaborate structure, such as a reinforced ring with flanges 142 protruding into the central opening 128 of the ring member 44. (FIGS. 29, 30, 32.)

In a preferred embodiment, the connector 130 has a conical tip 131 attached to a cylindrical portion 133 behind the tip 131 to which a suture 88 may attach. This embodiment is referred to as the arrowhead connector 132. (FIG. 32.) The cylindrical portion 133 behind the tip 131 has a smaller circumference than the widest part of the conical tip 131, such that there is a substantially flat shoulder 129 behind the tip 131. Accordingly, the arrowhead connector 132 is adapted for cooperating with the reinforced ring member 44 having flanges 142 that protrude into the central opening 128. As the tip 131 penetrates the central opening 128, the flanges 142 move aside, allowing passage of the tip 131. However, once the entire conical portion of the tip 131 has passed through the central opening 128, the flanges 142 return to their initial orientation around the central opening 128 and rest against the shoulder 129, resisting retrograde movement of the connector 130 through the ring member 44. (FIGS. 22, 23, 30, 32.) Since the cylindrical portion 133 behind the shoulder 129 of the arrowhead connector 132 has a means for connecting to a suture 88, the passage of the connector 130 through the ring member 44 creates a connection between the suture 88 and the sling 42. By this method of connecting suture 88 to sling 42, there is no need for stitching or tying knots to the sling 42, which greatly simplifies and accelerates the securing procedure.

Another preferred embodiment of the securing device 126 has a connector 130 with two perpendicular cylindrical members 135, 137 wherein the members 135, 137 are substantially flexibly attached one to the other at a flexible joint 139. (FIG. 34.) The rear cylinder 135 has a means of attaching to a suture 88, while the leading cylinder 137 is adapted for passage through the ring member 44. As this embodiment of the connector 130, referred to herein as the T connector 134, is inserted into a cannula 90 for advancement toward the sling 42, the perpendicularity between the two cylindrical members 135, 137 is distorted, and the leading cylinder 137 assumes a position that is more closely parallel, rather than perpendicular, to the rearward cylinder 135. (FIG. 35.) However, after the T connector 134 has passed through the cannula 90 and the leading cylinder 137 of the T connector 134 has also passed through the ring member 44 of the sling 42, the angular relationship between the two cylindrical members 135, 137 reverts to perpendicular. (FIG. 33.) In this conformation, the connector 130 may not pass back through the ring member 44, and a secure connection between the suture 88 and the sling 42 is therefore established.

This aspect of the invention provides a method for simple, minimally invasive placement and securing of a sling 42 in a tissue cavity. A tissue cavity, such as a cavity in the hiatal tissue, is created by use of, for example, the dilator 10 or the incision guide 50 of the invention. Alternatively an existing tissue cavity, such as the vagina 4, may be selected for placement of the sling 42. In addition, a tissue cavity in the hiatal tissue may be created by inserting a dilator 10 or an incision guide 50 through the upper vaginal wall 8. A sling 42 is then placed into the cavity in its desired location. This step is preferably performed with the use of the insert card 30 of the invention, wherein the insert card 30 carries and supports the sling 42 in its appropriate position within the cavity until it secured there. (FIG. 18.)

Figure 20:
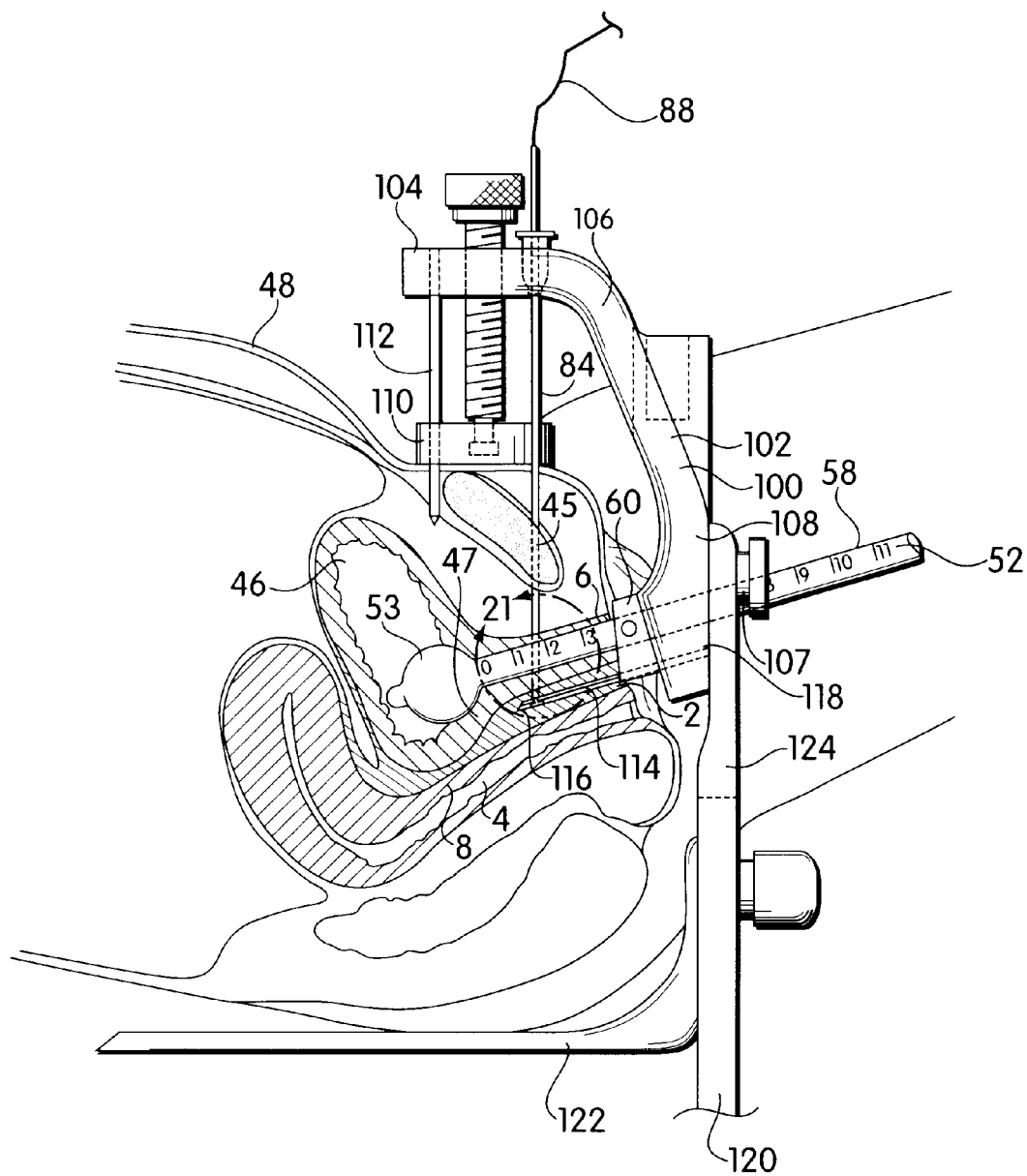
FIG. 20 corresponds to FIG. 19, but shows the driver frame with the cannula in place and a suture with quick-connect device passing through the cannula.

A cannula 90 is driven through the pubic bone using, for example, either the driver 70 of the invention or the driver frame assembly 100 of the invention. (FIG. 18.) The cannula 90 is then further driven through tissue until it approaches and aligns with the sling 42, (FIG. 19.) which is equipped with ring members 44. A connector 130 attached to the suture 88 is then inserted into the lumen of the cannula 90 and advanced therethrough until it contacts with and passes through the ring member 44 of the sling 42. (FIGS. 20, 21, 22.) At this point, the suture 88 is tested for the integrity of the connection between the connector 130 and the ring member 44, and the cannula 90 is withdrawn from the pubic bone. The suture 88 may then be appropriately tensioned and secured to the pubic bone (FIG. 28) as will be discussed below. Also contemplated as embodiments of this aspect of the invention are similar connections between other kinds of medical devices and suture 88 via, for example, arrowhead connector 132 or T connector 134 passing through a cannula 90 which has been driven through the pubic bone.

As a further embodiment of the present invention, the securing devices 126 of the invention may be used to secure a urethral sling 42 or other medical device after such a device has been positioned in a tissue cavity that was created transvaginally. For example, a cavity may be opened in the upper vaginal wall 8 by hydrodissection, or by means of the spreader 12 of the invention, or by blunt dissection. A medical device such as a urethral sling 42 may then be placed into the cavity, wherein the medical device has one or more ring members 44 capable of permitting unidirectional passage of a connector 130 of the securing device 126. The appropriate connector 130 is then passed through the corresponding ring member 44, and the device is secured in place in the transvaginally created tissue pocket. (See FIG. 23.)

Figure 31:
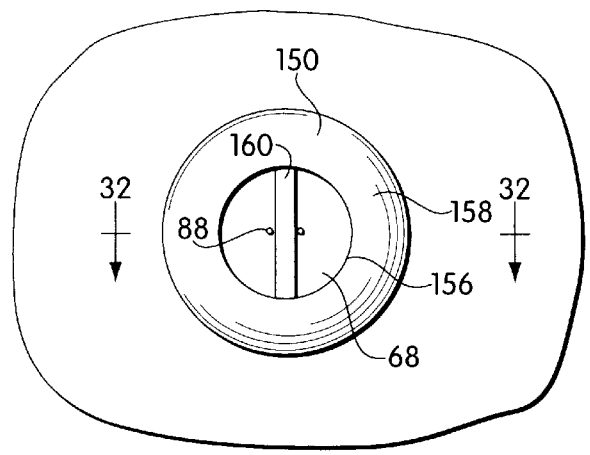
FIG. 31 is a plan view showing the bone eyelet in position in a bone with suture on either side of the crosspiece.

This invention is further characterized by a bone eyelet 150 for securing suture 88 to a bone. The bone eyelet 150 consists of a sleeve 152 and at least one crosspiece 160. (FIG. 31.) The sleeve 152 has an outer surface 154 that is adapted for inserting into and contacting with a bone, and also has an inner surface 156 such that the sleeve 152 is a substantially hollow structure with openings at either end. (FIG. 32a.) The crosspiece 160 is attached to the inner surface 156 of the sleeve 152, and creates a plurality of channels within the sleeve 152.

Several alternative embodiments of the bone eyelet 150 are contemplated in the present invention. In one preferred embodiment, the crosspiece 160 is a single rod 164. (FIG. 33.) In another preferred embodiment, the crosspiece 160 is a plane 162. (FIG. 32.) In both of these embodiments, the presence of the single crosspiece 160 produces two channels 168 through which a suture 88 may pass. In another embodiment, the crosspiece 160 is created by crimping or piercing the sleeve 152. In this embodiment, the thus-distorted portion of the sleeve 152 becomes the crosspiece 160, as shown in FIG. 32. In other embodiments, multiple crosspieces 160 may be present in the sleeve 152, to produce more than two channels 168 through which a suture 88 may pass. In another embodiment, the sleeve 152 includes a perpendicular flange rim 158. This flange rim 158 suspends the sleeve 152 at the surface of the bone and prevents it from sliding into the hole in the bone. (FIGS. 31–33.)

This aspect of the invention provides a method for securing a suture 88 to a bone. In this method, a suture 88 is passed through a bone in which a path for suture 88 has been created, for example, by driving a bone-piercing guide 84 according to this invention. Where two ends of a suture 88 both extend past the surface of the bone, each end may be advanced through one of the channels 168 among the plurality of channels 168 provided in the bone eyelet 150. The suture 88 ends may then be tied together and will be prevented from sliding into the bone by the action of the crosspiece 160 of the bone eyelet 150. (See FIGS. 32, 33.)

Another embodiment of this method includes a step of tensioning the suture 88 during the tying step to achieve a desired elevation of the structures to which the suture 88 is attached. For example, this method may be employed in connection with a securing device 126 discussed above to greatly accelerate and simplify the steps in securing a tissue mass or a urethral sling 42 in a tissue cavity. (FIGS. 32, 33.) Accordingly, the bone eyelet 150 may be used in connection with the driver 70 aspect of the this invention, as well as the driver frame assembly 100 aspect of the invention. It may further be adapted for use with other means of advancing a suture 88 through a pubic bone.

Figure 36:
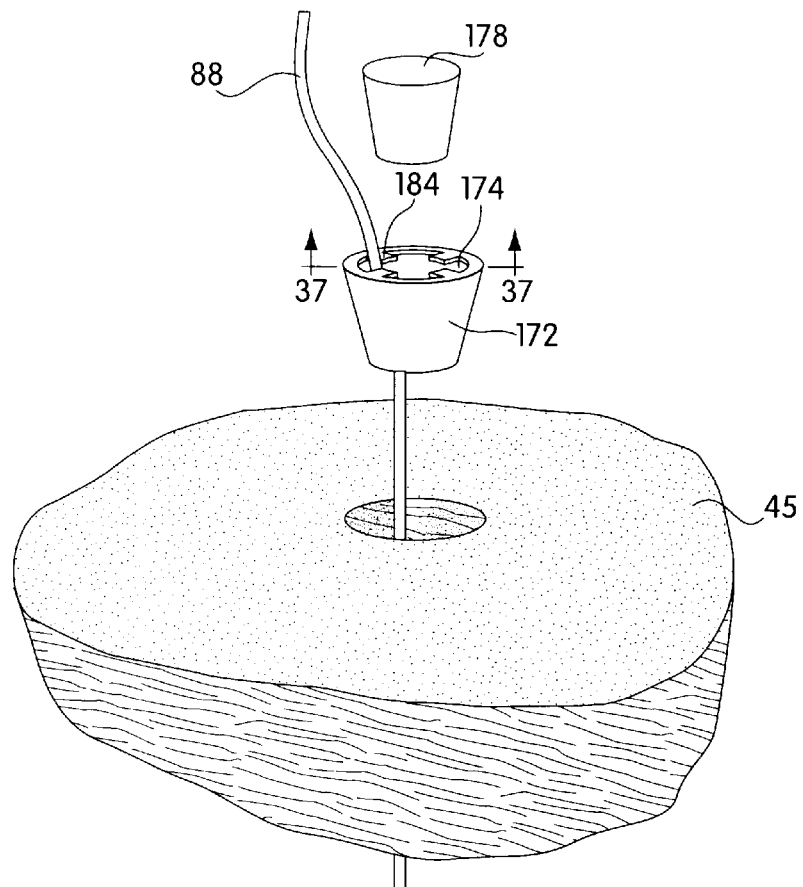
FIG. 36 is a perspective view of a bone suture fastener and a sleeve plug oriented above the pubic bone.
Figure 37A:
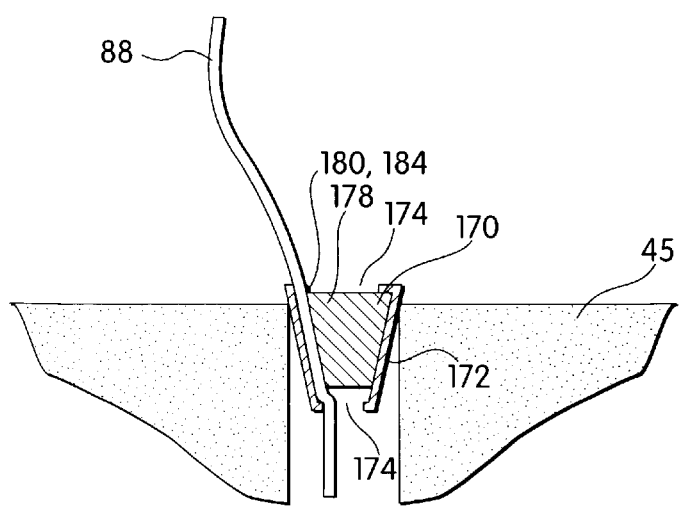
FIG. 37a is a cross-section taken along the line 37—37 in FIG. 36 and illustrates suture passing through the sleeve with the sleeve plug in place.
Figure 37B:
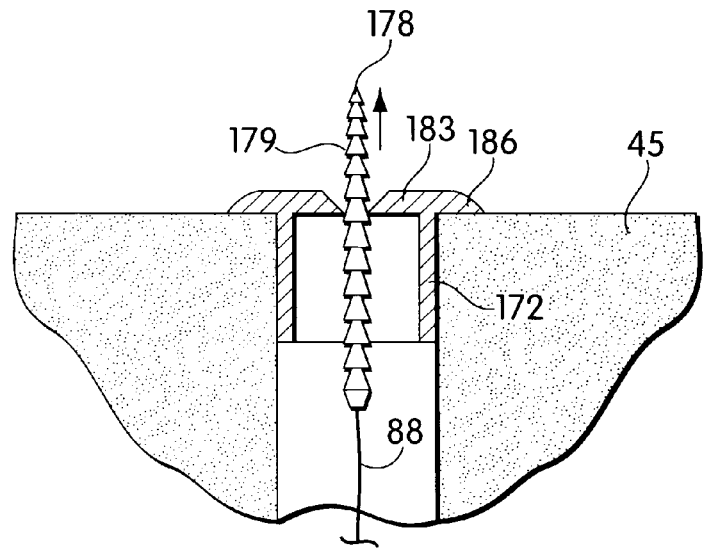
FIG. 37b is a cross section view similar to FIG. 37a showing the zipper-lock configuration of the bone suture fastener with the sleeve plug in place.
Figure 38:
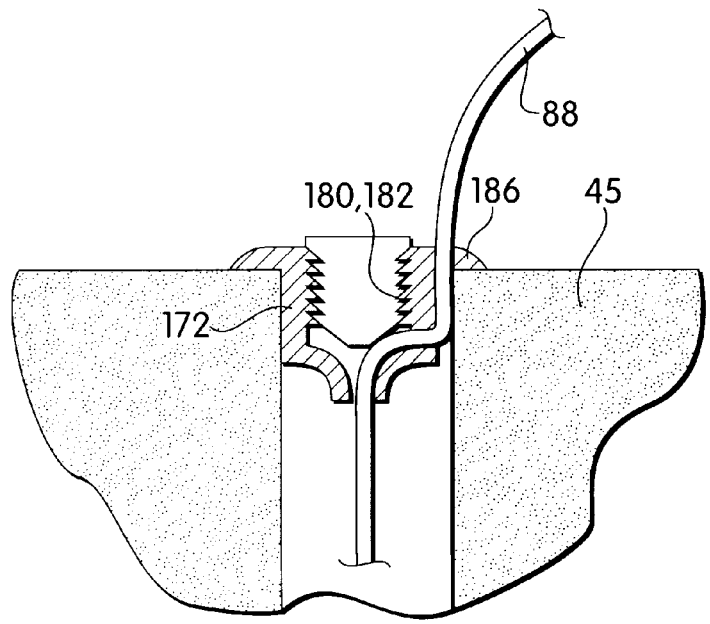
FIG. 38 is a cross section view similar to FIG. 37a showing the threaded configuration of the bone suture fastener with the sleeve plug in place.

A further aspect of the present invention provides a bone suture fastener 170 for quick and simplified connection of a suture 88 to a bone. (FIGS. 36–38.) The suture fastener 170 consists of a sleeve 172 having an opening 174 at each end, and a sleeve plug 178. The sleeve 172 is provided with a friction surface 180 for contacting the sleeve plug 178 and for preventing disengagement of the plug 178 from the sleeve 172. Different embodiments of the bone suture fastener 170 have a sleeve 172 that is substantially conical or cylindrical and a sleeve plug 178 that is likewise substantially conical or cylindrical. In one embodiment the friction surface 180 is a plurality of friction flanges 184 partially occluding one opening 174 of the suture fastener sleeve 172. (FIGS. 36, 37a.) These flanges 184 flex is one direction to allow insertion of the sleeve plug 178 into the sleeve 172 and then prevent release of the sleeve plug 178 from the sleeve 172. In another embodiment, the friction surface 180 is threaded 182 and the sleeve 172 is substantially cylindrical. (FIG. 38.) The sleeve plug 178 is likewise threaded 182 and is adapted for frictionally contacting the threads 182 of the suture fastener sleeve 172. An additional embodiment, the sleeve plug 178 may have a series of distortable angled rings 179 along its length, wherein the circumference of the top of each ring 179 is smaller than the circumference of the bottom of the same ring 179. The suture 88 may be tied directly to the sleeve plug 178. In this embodiment, the friction surface 180 of the sleeve 172 has a rim 183 adapted to allow unidirectional passage of the sleeve plug 178 and to prevent retrograde passage thereof, resulting in a one-way zipper-lock action. This embodiment allows a surgeon to adjust the tension on the suture 88 simply by pulling the sleeve plug 178 through the sleeve 172 to the desired position. (FIG. 37b.) In any of these embodiments, a flange rim 186 may extend around the circumference of one end of the sleeve 172 to prevent sinking of the bone suture fastener 170 past the surface of the bone. (FIG. 38.)

This aspect of the invention provides a method for quick and simple securing of a suture 88 that has passed through a bone. According to the method, one or multiple ends of a suture 88 may be passed through the sleeve 172 of the suture fastener 170 and the suture fastener 170 may be advanced along the suture 88 until it contacts the bone through which the suture 88 passes. (FIG. 36.) The sleeve 172 is secured in the bone near the bone surface either by a friction surface 180 on the outside of the sleeve 172, or by a flange rim 186 extending around the circumference of one end of the sleeve 172. With the sleeve 172 in place, and the suture 88 passing therethrough, the suture 88 may be tensioned to approximately the desired tension and the sleeve plug 178 partially inserted into the opening 174 of the sleeve 172 at the surface of the bone. Any desired tensioning or release of tension in the suture 88 is done prior to final seating of the sleeve plug 178 in the sleeve 172 against the friction surface 180. (FIGS.

37a and 38.) When the sleeve plug 178 is appropriately seated against the friction surface 180, the suture 88 is secured in place at the surface of the bone, and excess suture 88 is cut off by the surgeon.

Figure 28:
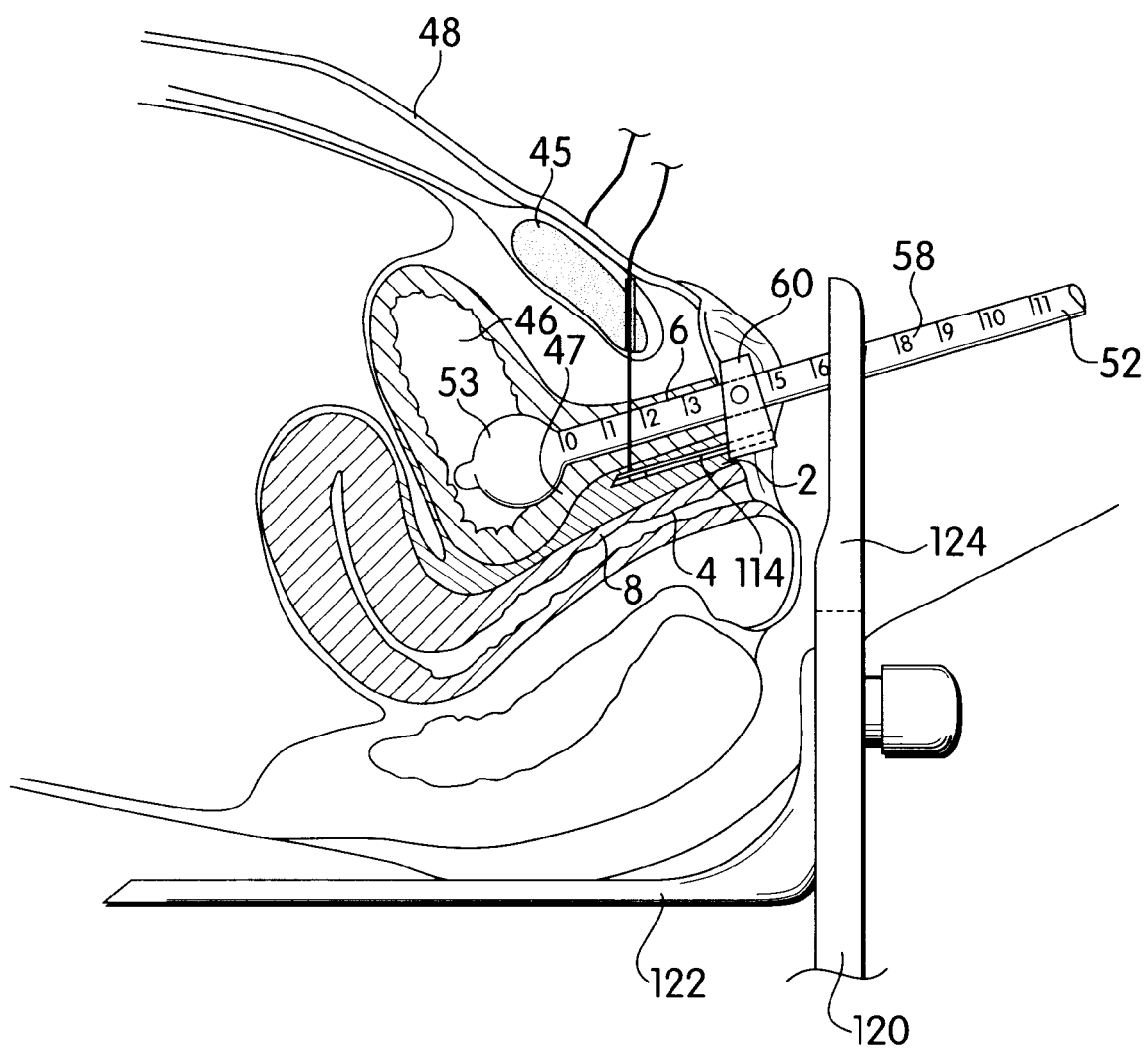
FIG. 28 is a cross section view as in FIG. 3 showing a sling with the ring member of a quick-connect device in place.

Another embodiment of this aspect of the invention contemplates the use of the bone suture fastener 170 to secure a suture 88 that is connected to a device or a stitch 92 in a transvaginally created tissue cavity. For example, a tissue cavity is dissected between the urethra and the upper vaginal wall 8 by hydrodissection, blunt instrument dissection, or by the spreader 12 of the invention. Subsequently, a sling 42 or other medical device may be placed in the cavity, or a suture 88 may be passed through a tissue mass to elevate or stabilize the tissue mass (compare FIG. 27a to FIG. 27b and note distance of elevation B, see also FIGS. 9, 10, 26). In cases where the suture 88 is passed through the tissue and follows a path through the pubic bone, the end of the suture 88 that protrudes from the pubic bone may be anchored thereto by means of the bone suture fastener 170 of this aspect of the invention. (FIG. 28.)

This method of the invention may be practiced in cooperation with several other methods and devices of the present invention. In any aspect of the invention in which a suture 88 is passed through a bone, the suture 88 may be advantageously secured to the bone in this manner. Thus, the quick connect bone suture fastening may be used in coordination with the quick connect securing devices 126 used to connect a sling 42 or other internally placed medical device with a suture 88. They also may be used to secure the ends of a suture 88 that has been passed through a tissue mass by stitching 92. They also may be used in connection with the bone-piercing guide driver 70 or with the driver frame assembly 100 of the invention.

Accordingly, the several aspects of the present invention cooperate to achieve the desired effect of providing a variety of surgical options for and solutions to problems associated with stress urinary incontinence and related dysfunctions or deformations of the urethral or pelvic floor. Also contemplated within the overall scope of the present invention are other applications for securing a soft target tissue to a relatively fixed reference tissue, such as the pubic bone. It is understood that the examples of embodiments and methods provided herein are merely representative of the invention, and are not taken to limit the invention beyond the express limitations of the following claims.

What is claimed is:

1. A dilator for creating a cavity, comprising:
   an insertion spreader comprising a first elongate semi-cylindrical spreader guide and a second elongated semi-cylindrical spreader guide, said first and second guides each having a distal end and a proximal end, said first and second guides being sharpened at said distal ends, said first guide being parallel to said second guide, said guides of said insertion spreader being movable between a closed position and an open position;
   a first and a second handle, each of said handles having a first end and a second end, wherein said first end of said first handle is attached to said first guide, said first end of said second handle is attached to said second guide, wherein the longitudinal axis of said first and second handles is substantially perpendicular to the longitudinal axis of said first and second guides, respectively, and said second end of each of said handles is adapted to allow a person to grasp and manipulate said dilator; and
   a pivot intermediate said first end and said second end of each of said handles, said handles being movably connected at said pivot, whereby movement of said handles about said pivot causes a displacement of said guides to move said guides between said closed and said open positions.

2. The dilator of claim 1 further comprising a ratcheting lock for maintaining said insertion spreader in a fixed position.

3. The dilator of claim 1, wherein said second ends of said handles comprise finger loops for grasping and manipulating said dilator.

4. The dilator of claim 1, wherein said first and second spreader guides generally form a cylinder when in placed in the closed position.

5. The dilator of claim 1, wherein said the separation of said first and second spreader guides in the open position is approximately 2.5 to 4 cm.

* * * * *